US012740802B2

(12) United States Patent
Hunter et al.

(10) Patent No.: US 12,740,802 B2
(45) Date of Patent: Sep. 22, 2026

(54) ROTATABLE LINEAR ACTUATION MECHANISM

(71) Applicant: Cilag GmbH International, Zug (CH)

(72) Inventors: Morgan R. Hunter, Cincinnati, OH (US); Brian D. Black, Loveland, OH (US); Thomas B. Remm, Milford, OH (US)

(73) Assignee: Cilag GmbH International, Zug (CH)

( * ) Notice: Subject to any disclaimer, the term of this patent is extended or adjusted under 35 U.S.C. 154(b) by 492 days.

(21) Appl. No.: 18/331,988

(22) Filed: Jun. 9, 2023

(65) Prior Publication Data

US 2023/0310022 A1 Oct. 5, 2023

Related U.S. Application Data

(63) Continuation of application No. 16/556,727, filed on Aug. 30, 2019, now Pat. No. 11,712,261.

(51) Int. Cl.
*A61B 17/32* (2006.01)
*A61B 17/00* (2006.01)

(52) U.S. Cl.
CPC ................ *A61B 17/320092* (2013.01); *A61B 17/320068* (2013.01); *A61B 2017/00367* (2013.01); *A61B 2017/320075* (2017.08); *A61B 2017/320094* (2017.08); *A61B 2017/320095* (2017.08)

(58) Field of Classification Search
CPC .... A61B 17/320092; A61B 17/320068; A61B 2017/320094; A61B 2017/320095; A61B 2017/320075; A61B 2017/00367
See application file for complete search history.

(56) References Cited

U.S. PATENT DOCUMENTS

| | | | |
|---|---|---|---|
| 5,322,055 | A | 6/1994 | Davison et al. |
| 5,873,873 | A | 2/1999 | Smith et al. |
| 5,980,510 | A | 11/1999 | Tsonton et al. |
| 6,325,811 | B1 | 12/2001 | Messerly |
| 6,500,176 | B1 | 12/2002 | Truckai et al. |
| 6,773,444 | B2 | 8/2004 | Messerly |
| 6,783,524 | B2 | 8/2004 | Anderson et al. |
| 7,112,201 | B2 | 9/2006 | Truckai et al. |
| 7,125,409 | B2 | 10/2006 | Truckai et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,220,951 | B2 | 5/2007 | Truckai et al. |

(Continued)

OTHER PUBLICATIONS

U.S. Appl. No. 61/410,603, entitled "Energy-Based Surgical Instruments," filed Nov. 5, 2010.

*Primary Examiner* — Ashley L Fishback
(74) *Attorney, Agent, or Firm* — FBT Gibbons LLP

(57) ABSTRACT

A surgical instrument includes an end effector, a shaft assembly proximally extending from the end effector, and at least one translatable rack gear assembly coupled with the shaft assembly. The shaft assembly includes at least one elongate member connected to a select one or both of the end effector and the shaft assembly. The at least one translatable rack gear assembly includes a rack gear, an anchor longitudinally adjustable relative to the rack gear, and an insert received within the anchor. The anchor is coupled with the at least one elongate member such that adjustment of the anchor relative to the rack gear longitudinally moves the insert and the at least one elongate member for adjusting tension of the at least one elongate member.

20 Claims, 16 Drawing Sheets

(56) References Cited

U.S. PATENT DOCUMENTS 7,309,849 B2 12/2007 Truckai et al.
7,311,709 B2 12/2007 Truckai et al.
7,354,440 B2 4/2008 Truckai et al.
7,381,209 B2 6/2008 Truckai et al.
8,461,744 B2 6/2013 Wiener et al.
8,479,969 B2 7/2013 Shelton, IV
8,573,461 B2 11/2013 Shelton, IV et al.
8,573,465 B2 11/2013 Shelton, IV
8,591,536 B2 11/2013 Robertson
8,602,288 B2 12/2013 Shelton, IV et al.
8,616,431 B2 12/2013 Timm et al.
8,623,027 B2 1/2014 Price et al.
8,663,220 B2 3/2014 Wiener et al.
8,783,541 B2 7/2014 Shelton, IV et al.
8,800,838 B2 8/2014 Shelton, IV
8,820,605 B2 9/2014 Shelton, IV
8,844,789 B2 9/2014 Shelton, IV et al.
8,911,460 B2 12/2014 Neurohr et al.
9,023,071 B2 5/2015 Miller et al.
9,095,367 B2 8/2015 Olson et al.
9,301,759 B2 4/2016 Spivey et al.
9,381,058 B2 7/2016 Houser et al.
9,393,037 B2 7/2016 Olson et al.
9,402,682 B2 8/2016 Worrell et al.
9,949,785 B2 4/2018 Price et al.
10,034,683 B2 7/2018 Monroe et al.
10,172,636 B2 1/2019 Stulen et al.
10,226,274 B2 3/2019 Worrell et al.
10,342,567 B2 7/2019 Hibner et al.
11,457,945 B2 10/2022 Hunter et al.
11,471,181 B2 10/2022 Hunter et al.
11,612,409 B2 3/2023 Black et al.
11,712,261 B2 8/2023 Hunter et al.
2006/0079874 A1 4/2006 Faller et al.
2007/0191713 A1 8/2007 Eichmann et al.
2007/0282333 A1 12/2007 Fortson et al.
2008/0200940 A1 8/2008 Eichmann et al.
2011/0087212 A1 4/2011 Aldridge et al.
2012/0116265 A1 5/2012 Houser et al.
2015/0320438 A1 11/2015 Weisenburgh, II et al.
2016/0302818 A1 10/2016 Weisenburgh, II et al.
2016/0302819 A1 10/2016 Stulen et al.
2017/0281217 A1 10/2017 Hibner
2017/0281218 A1 10/2017 Timm
2017/0281219 A1 10/2017 Hibner et al.
2017/0281220 A1 10/2017 Hibner et al.
2017/0281221 A1 10/2017 Boudreaux
2021/0059709 A1 3/2021 Black et al.
2021/0059711 A1 3/2021 Hunter et al.

14
10
16
44
48
52
61
46
51
50
62
70
82
86
72
74
72
64
86
72
86
68
60
58
84
80
78
56
80
78
80
78
76
80
78

206b
106
63
206c
106
206d
106
63
206e
106
206f
106
92
60

206b
106
220
206c
220
106
206d
220
106
206e
220
230
106
63
74
206f
230
63
106
74
220
92
60

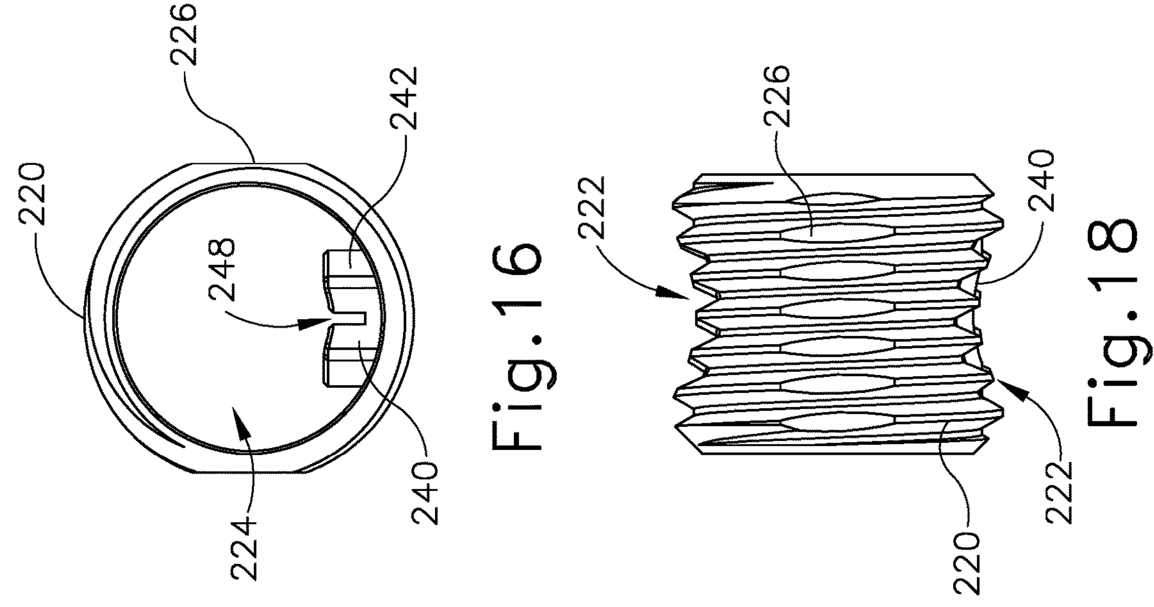
Fig.16
Fig.18
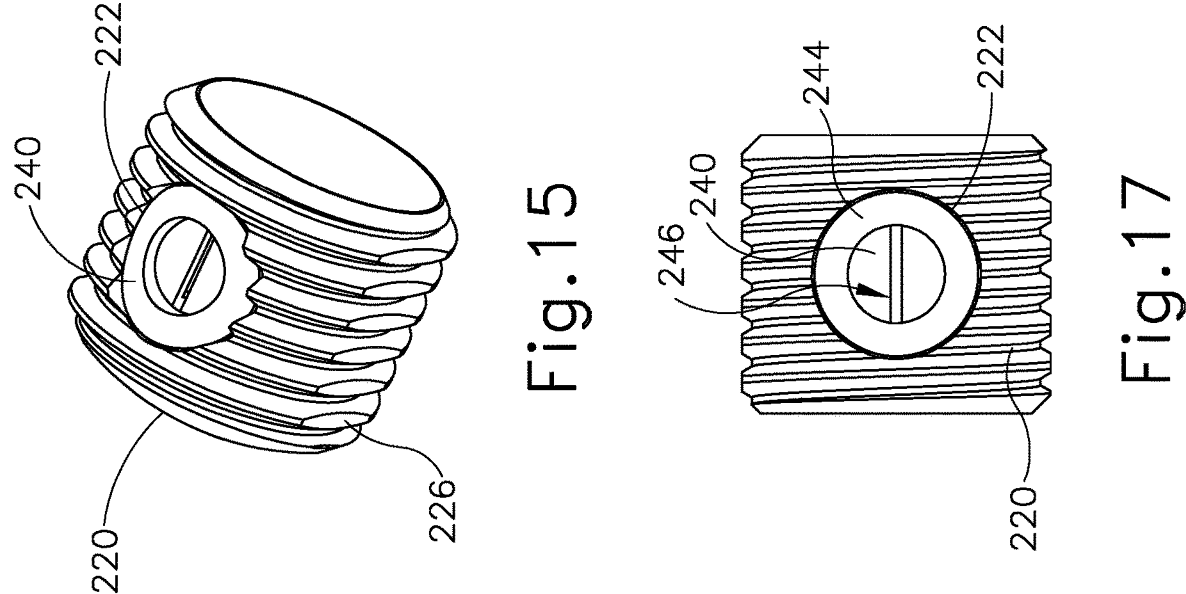
Fig.15
Fig.17

216
213
216
211
216
106
216
216
214

211
106
216

213
211
106
214
216

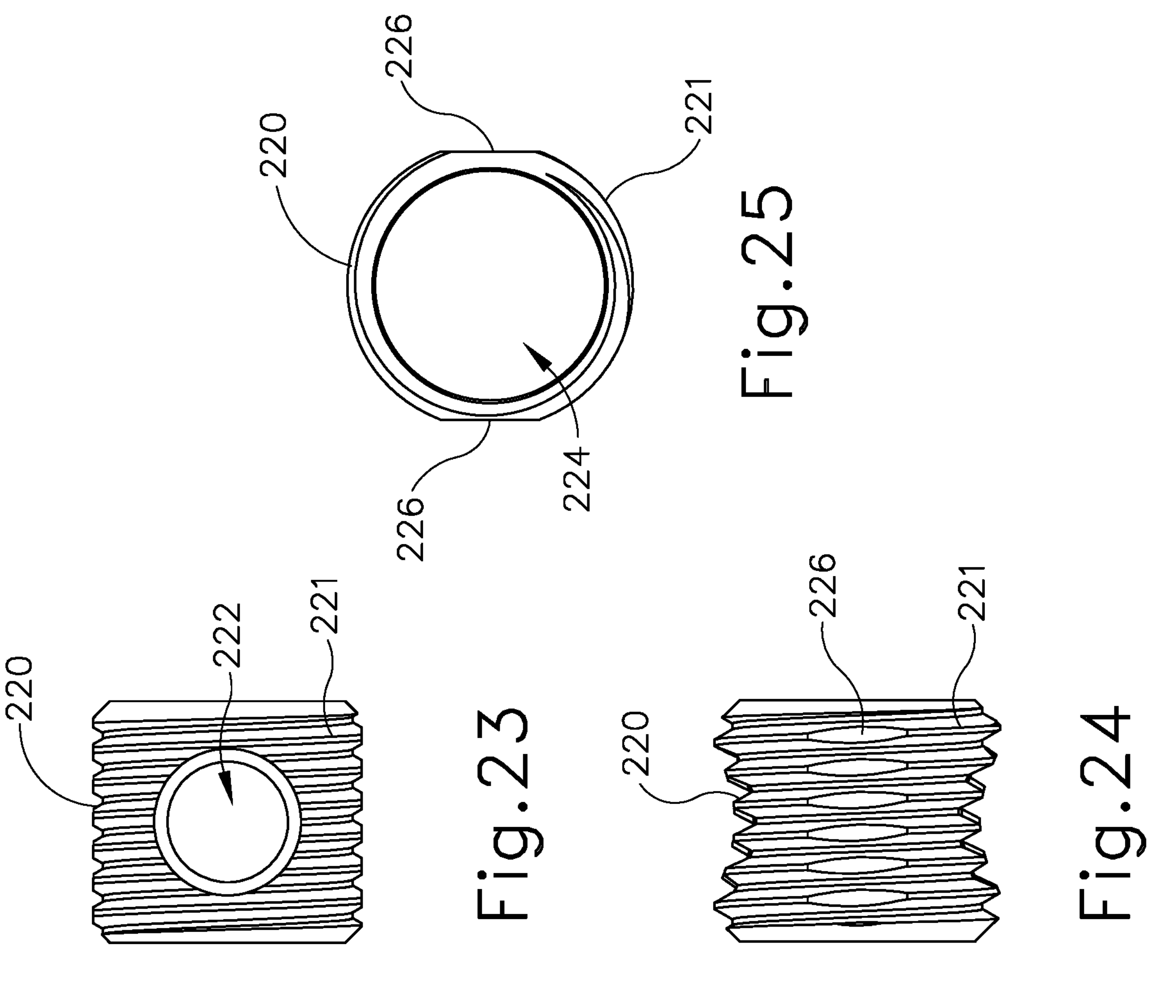
Fig.25
Fig.23
Fig.24
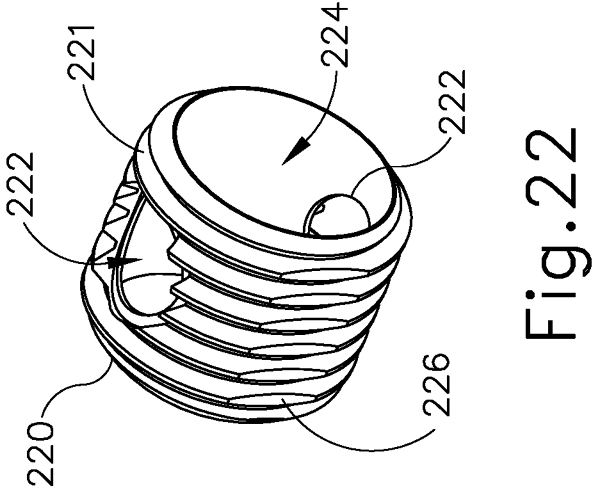
Fig.22

240
244
242
Fig.27
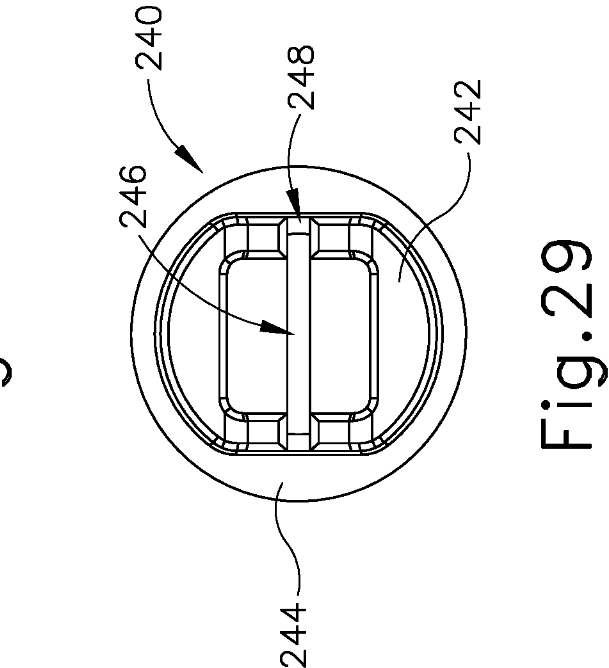
Fig.29
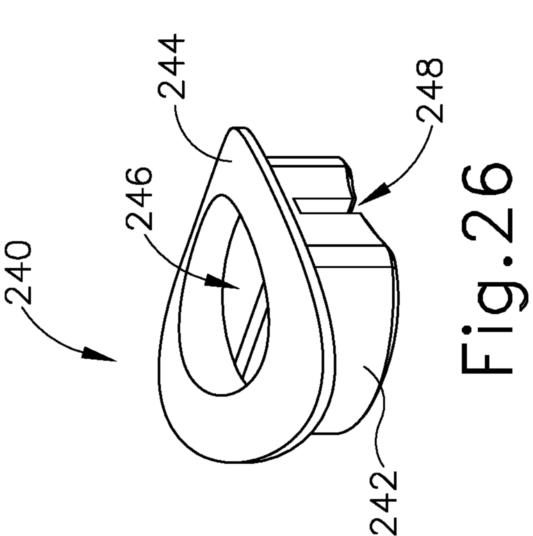
Fig.26
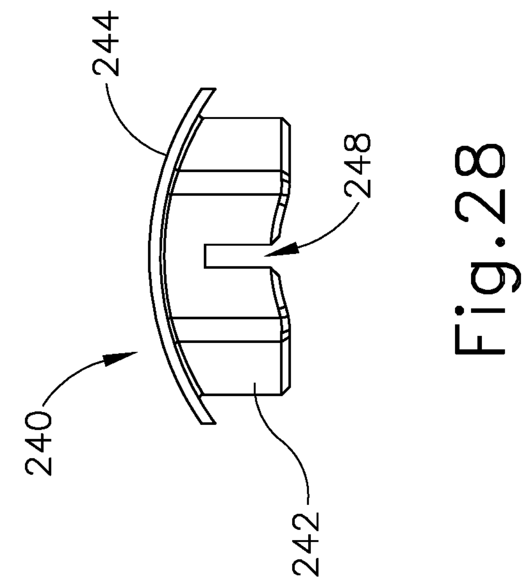
Fig.28

ROTATABLE LINEAR ACTUATION MECHANISM

PRIORITY

This application is a continuation of U.S. patent application Ser. No. 16/556,727, entitled "Rotatable Linear Actuation Mechanism," filed Aug. 30, 2019, published as U.S. Pub. No. 2021/0059711 on Mar. 4, 2021, issued as U.S. Pat. No. 11,712,261 on Aug. 1, 2023.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element.

Such surgical instruments may be directly gripped and manipulated by a surgeon or incorporated into a robotically assisted surgery. During robotically assisted surgery, the surgeon typically operates a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller typically includes one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein; and U.S. Pat. No. 8,911,460, entitled "Ultrasonic Surgical Instruments," issued Dec. 16, 2014, the disclosure of which is incorporated by reference herein; and U.S. Pat. No. 9,023,071, entitled "Ultrasonic Device for Fingertip Control," issued May 5, 2015, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pat. No. 9,023,071, entitled "Ultrasonic Device for Fingertip Control," issued May 5, 2015, the disclosure of which is incorporated by reference herein.

Some ultrasonic surgical instruments may include a cordless transducer such as that disclosed in U.S. Pat. No. 9,381,058, entitled "Recharge System for Medical Devices," issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pat. No. 9,393,037, issued Jul. 19, 2016, entitled "Surgical Instruments with Articulating Shafts," the disclosure of which is incorporated by reference herein; U.S. Pat. No. 9,095,367, issued Aug. 4, 2015, entitled "Flexible Harmonic Waveguides/Blades for Surgical Instruments," the disclosure of which is incorporated by reference herein; U.S. Pat. No. 10,226,274, issued Mar. 12, 2019, entitled "Ultrasonic Surgical Instrument with Articulation Joint Having Plurality of Locking Positions," the disclosure of which is incorporated by reference herein; U.S. Pat. No. 10,034,683, entitled "Ultrasonic Surgical Instrument with Rigidizing Articulation Drive Members," issued Jul. 31, 2018, the disclosure of which is incorporated by reference herein; U.S. Pat. Pub.

No. 2016/0302818, published Oct. 10, 2016, now abandoned, entitled "Ultrasonic Surgical Instrument with Movable Rigidizing Member," the disclosure of which is incorporated by reference herein; U.S. Pat. Pub. No. 2016/0302819, published Oct. 20, 2016, now abandoned, entitled "Ultrasonic Surgical Instrument with Articulating End Effector having a Curved Blade," the disclosure of which is incorporated by reference herein; U.S. Pat. No. 10,342,567, issued Jul. 9, 2019, entitled "Ultrasonic Surgical Instrument with Opposing Thread Drive for End Effector Articulation," the disclosure of which is incorporated by reference herein; U.S. Pat. Pub. No. 2015/0320438, published Nov. 12, 2015, issued as U.S. Pat. No. 10,667,835 on Jun. 2, 2020, entitled "Ultrasonic Surgical Instrument with End Effector Having Restricted Articulation," the disclosure of which is incorporated by reference herein; U.S. Pat. Pub. No. 2017/0281217, published Oct. 5, 2017, issued as U.S. Pat. No. 10,492,819 on Dec. 3, 2019, entitled "Surgical Instrument with Dual Mode Articulation Drive," the disclosure of which is incorporated by reference herein; U.S. Pat. Pub. No. 2017/0281218, published Oct. 5, 2017, issued as U.S. Pat. No. 10,507,034 on Dec. 17, 2019, entitled "Surgical Instrument with Motorized Articulation Drive in Shaft Rotation Knob," the disclosure of which is incorporated by reference herein; U.S. Pat. Pub. No. 2017/0281219, published Oct. 5, 2017, issued as U.S. Pat. No. 10,743,850 on Aug. 18, 2020, entitled "Surgical Instrument with Locking Articulation Drive Wheel," the disclosure of which is incorporated by reference herein; U.S. Pat. Pub. No. 2017/0281220, published Oct. 5, 2017, issued as U.S. Pat. No. 10,575,836 on Mar. 3, 2020, entitled "Surgical Instrument with Selectively Locked Articulation Assembly," the disclosure of which is incorporated by reference herein; and U.S. Pat. Pub. No. 2017/0281221, published Oct. 5, 2017, issued as U.S. Pat. No. 10,405,876 on Sep. 10, 2019, entitled "Articulation Joint for Surgical Instrument," the disclosure of which is incorporated by reference herein.

Some instruments are operable to seal tissue by applying radiofrequency (RF) electrosurgical energy to the tissue. An example of a surgical instrument that is operable to seal tissue by applying RF energy to the tissue is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein; and U.S. Pat. No. 8,663,220, entitled "Ultrasonic Surgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 15 depicts a perspective view of the translatable rack gear assembly of FIG. 13 with a rack gear removed for greater clarity;

FIG. 16 depicts a side elevational view of the translatable rack gear assembly of FIG. 15;

FIG. 17 depicts a front view of the translatable rack gear assembly of FIG. 15;

FIG. 18 depicts a top plan view of the translatable rack gear assembly of FIG. 15;

FIG. 22 depicts a perspective view of an anchor of the translatable rack gear assembly of FIG. 7;

FIG. 23 depicts a front view of the anchor of FIG. 22;

FIG. 24 depicts a top plan view of the anchor of FIG. 22;

FIG. 25 depicts a side elevational view of the anchor of FIG. 22;

FIG. 26 depicts a perspective view of the drive band insert of the translatable gear assembly of FIG. 7;

FIG. 27 depicts a front view of the drive band insert of FIG. 26;

FIG. 28 depicts a side elevational view of the drive band insert of FIG. 26;

FIG. 29 depicts a top plan view of the drive band insert of FIG. 26;

Figure 1:
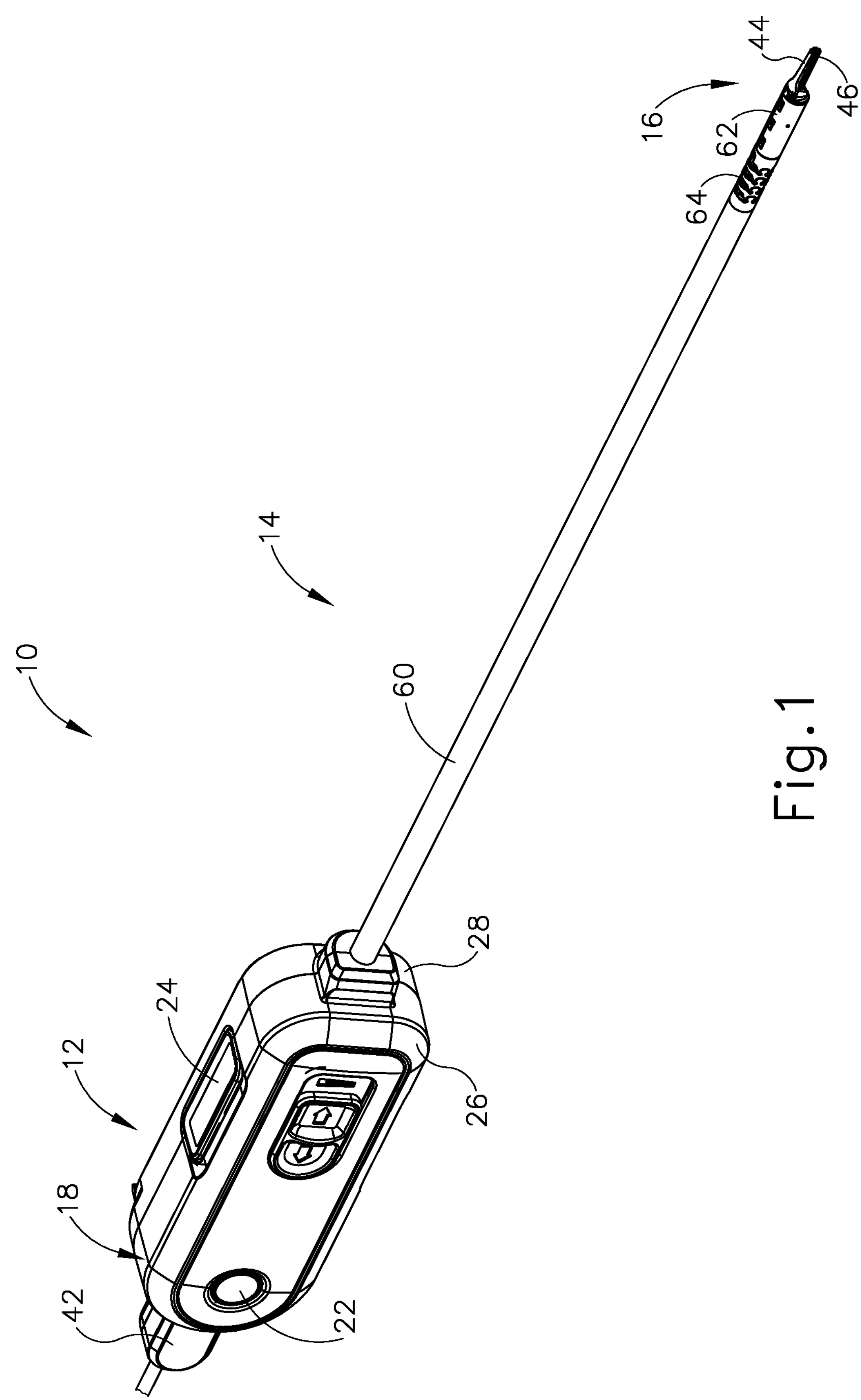
FIG. 1 depicts a front perspective view of an ultrasonic surgical instrument having an end effector, a shaft assembly, and a base assembly configured to connect to a robotic driven interface.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "front," "side," "top," "bottom," "rear," "clockwise," "counterclockwise," "longitudinal," and "transverse" also are used herein for reference to relative positions and directions. Such terms are used below with reference to views as illustrated for clarity and are not intended to limit the invention described herein.

I. Exemplary Surgical Instrument

FIG. 1 shows an exemplary surgical instrument, such as an ultrasonic surgical instrument (10). At least part of ultrasonic surgical instrument (10) may be constructed and operable in accordance with at least some of the teachings of any of the various patents, patent application publications, and patent applications that are cited herein. As described therein and as will be described in greater detail below, ultrasonic surgical instrument (10) is operable to cut tissue and seal or weld tissue (e.g., a blood vessel, etc.) substantially simultaneously. While the present example incorporates various ultrasonic features as ultrasonic surgical instrument (10), the invention is not intended to be unnecessarily limited to the ultrasonic features described herein.

Ultrasonic surgical instrument (10) of the present example comprises a body assembly, such as a base assembly (12), a shaft assembly (14), and an end effector (16). Base assembly (12) includes a housing (18), a button (22), and a pair of latch clasps (24). Button (22) is operatively connected to an electrical base power controller (not shown) and configured to selectively power ultrasonic surgical instrument (10) for use. In addition, housing (18) of the present example includes a front housing cover (26) and a rear housing cover (28) removably secured together via latch clasps (24). More particularly, latch clasps (24) removably secure front housing cover (26) to rear housing cover (28) such that front housing cover (26) may be removed for accessing an interior space (30) (see FIG. 5) within base assembly (12). Shaft assembly (14) distally extends from base assembly (12) to end effector (16) to thereby communicate mechanical and/or electrical forces therebetween for use as will be discussed below in greater detail. As shown in the present example, base assembly (12) is configured to operatively connect to a robotic drive (not shown) for driving various features of shaft assembly (14) and/or end effector (16). However, in another example, body assembly may alternatively include a handle assembly (not shown), which may include a pistol grip (not shown) in one example, configured to be directly gripped and manipulated by the surgeon for driving various features of shaft assembly (14) and/or end effector (16). The invention is thus not intended to be unnecessarily limited to use with base assembly (12) and the robotic drive (not shown).

Figure 2:
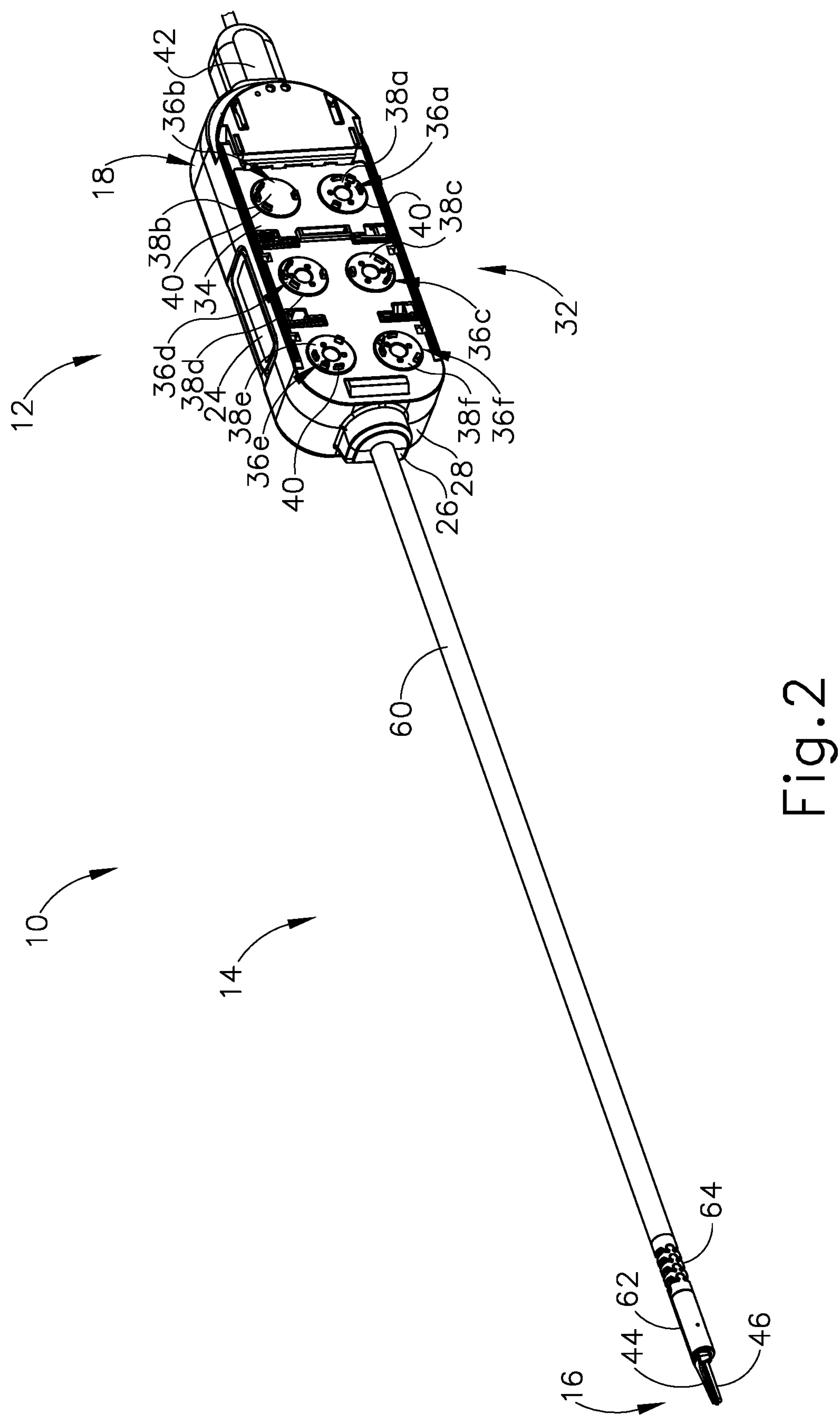
FIG. 2 depicts a rear perspective view of the ultrasonic surgical instrument of FIG. 1.

To this end, with respect to FIG. 2, base assembly (12) includes a robotic driven interface (32) extending through a base plate (34) of rear housing cover (28) and configured to mechanically couple with the robotic drive (not shown). Robotic driven interface (32) of the present example includes a plurality of instrument actuators (**36*a*, 36*b*, 36*c*, 36*d*, 36*e*, 36*f*) having a plurality of input bodies (38*a*, 38*b*, 38*c*, 38*d*, 38*e*, 38*f*), respectively. Each input body (38*a*, 38*b*, 38*c*, 38*d*, 38*e*, 38*f*), which may also be referred to herein as a "puck," is configured to removably connect with the robotic drive (not shown) and, in the present example, is generally cylindrical and rotatable about an axis. Input bodies (38*a*, 38*b*, 38*c*, 38*d*, 38*e*, 38*f*) have a plurality of slots (40) configured to receive portions of the robotic drive (not shown) for gripping and rotatably driving input bodies (38*a*, 38*b*, 38*c*, 38*d*, 38*e*, 38*f*) in order to direct operation of shaft assembly (14) and/or end effector (16) as will be discussed below in greater detail. Base assembly (12) also receives an electrical plug (42) operatively connected to an electrical power source (not shown) to provide electrical power to base assembly (12) for operation as desired, such as powering electrical base power controller (not shown) and directing electrical energy to various features of shaft assembly (14) or end effector (16**) associated with cutting, sealing, or welding tissue.

A. Exemplary End Effector and Acoustic Drivetrain

Figures 3A, 3B:
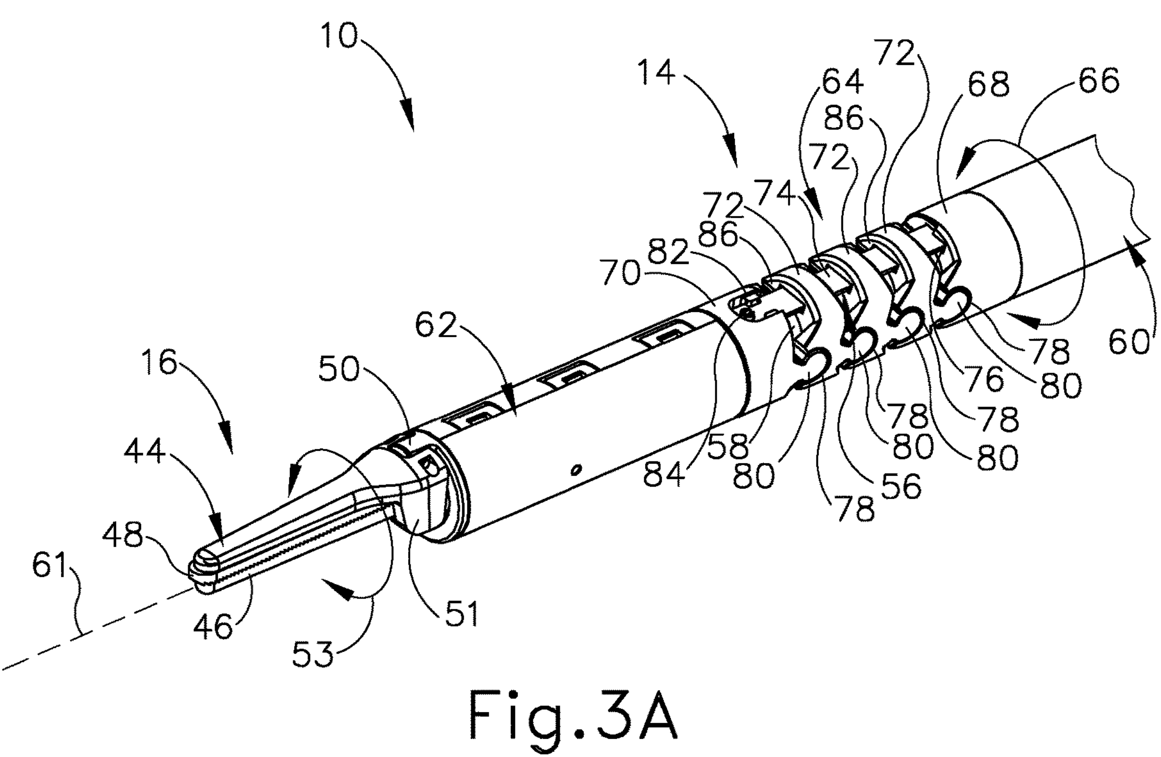
FIG. 3A depicts an enlarged perspective view of the ultrasonic surgical instrument of FIG. 1 with the end effector in a closed position and the shaft assembly in a straight configuration.
FIG. 3B depicts the enlarged perspective view of the ultrasonic surgical instrument similar to FIG. 3A, but showing the end effector in an open position.

As best seen in FIGS. 3A-3B, end effector (16) of the present example includes a clamp arm (44) and an ultrasonic blade (46). Clamp arm (44) has a clamp pad (48) secured to an underside of clamp arm (44), facing blade (46). In one example, clamp pad (48) may comprise polytetrafluoroethylene (PTFE) and/or any other suitable material(s). Clamp arm (44) is pivotally secured to a distally projecting tongue (50) of shaft assembly (14). Clamp arm (44) is operable to selectively pivot toward and away from blade (46) to selectively clamp tissue between clamp arm (44) and blade (46). A pair of arms (51) extend transversely from clamp arm (44) and are pivotally secured to another portion of shaft assembly (14) configured to longitudinally slide to pivot clamp arm (44) as indicated by an arrow (52) between a closed position shown in FIG. 3A and an open position shown in FIG. 3B.

In addition to pivoting relative to blade (46), clamp arm (44) of the present example is further configured to rotate about blade (46) relative to blade (46) and also relative to shaft assembly (14) as indicated by an arrow (53). In one example, clamp arm (44) rotates in the clockwise or counterclockwise directions completely around blade (46) and may be selectively fixed in any angular position relative to blade (46) for directing clamp arm (44) from the open position to the closed position for clamping tissue. In another example, clamp arm (44) may have rotational stops (not shown) configured to limit rotational movement of clamp arm (44) relative to blade (46) in one or more predetermined positions.

Blade (46) of the present example is operable to vibrate at ultrasonic frequencies in order to effectively cut through and seal tissue, particularly when the tissue is being compressed between clamp pad (48) and blade (46). Blade (46) is positioned at a distal end of an acoustic drivetrain. This acoustic drivetrain includes a transducer assembly (54) (see FIG. 5) and an acoustic waveguide (56), which includes a flexible portion (58) discussed below in greater detail. It should be understood that waveguide (56) may be configured to amplify mechanical vibrations transmitted through waveguide (56). Furthermore, waveguide (56) may include features operable to control the gain of the longitudinal vibrations along waveguide (56) and/or features to tune waveguide (56) to the resonant frequency of the system. Various suitable ways in which waveguide (56) may be mechanically and acoustically coupled with transducer assembly (54) (see FIG. 5) will be apparent to those of ordinary skill in the art in view of the teachings herein.

Those of ordinary skill in the art will understand that, as a matter of physics, a distal end of blade (46) is located at a position corresponding to an anti-node associated with resonant ultrasonic vibrations communicated through flexible portion (58) of waveguide (56). When transducer assembly (54) (see FIG. 5) is energized, the distal end of blade (46) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (54) (see FIG. 5) of the present example is activated, these mechanical oscillations are transmitted through waveguide (56) to reach blade (46), thereby providing oscillation of blade (46) at the resonant ultrasonic frequency. Thus, when tissue is secured between blade (46) and clamp pad (48), the ultrasonic oscillation of blade (46) may simultaneously sever the tissue and denature the proteins in adjacent tissue cells, thereby providing a coagulative effect with relatively little thermal spread. In some versions, end effector (16) is operable to apply radiofrequency (RF) electrosurgical energy to tissue in addition to applying ultrasonic energy to tissue. In any case, other suitable configurations for an acoustic transmission assembly and transducer assembly (54) will be apparent to one of ordinary skill in the art in view of the teachings herein. Similarly, other suitable configurations for end effector (16) will be apparent to those of ordinary skill in the art in view of the teachings herein.

B. Exemplary Shaft Assembly and Articulation Section

As shown in FIGS. 3A-3B, shaft assembly (14) includes a proximal shaft portion (60) extending along a longitudinal axis (61), a distal shaft portion (62) distally projecting relative to the proximal shaft portion (60), and an articulation section (64) extending between proximal and distal shaft portions (60, 62). Shaft assembly (14) is configured to rotate about longitudinal axis (61) as indicated by an arrow (66). In one example, shaft assembly (14) rotates in the clockwise or counterclockwise directions completely around longitudinal axis (61) and may be selectively fixed in any rotational position about longitudinal axis (61) for positioning articulation section (64) and/or end effector (16) about longitudinal axis (61). While end effector (16) generally rotates with shaft assembly (14) as indicated by arrow (66), end effector (16) may be simultaneously and independently rotated as indicated by arrow (53) relative to shaft assembly (14) during use for repositioning portions of shaft assembly (14) and/or end effector (16) as desired.

Articulation section (64) is configured to selectively position end effector (16) at various lateral deflection angles relative to longitudinal axis (61) defined by proximal shaft portion (60). Articulation section (64) may take a variety of forms. In the present example, articulation section (64) includes a proximal link (68), a distal link (70), and a plurality of intermediate links (72) connected in series between proximal and distal links (68, 70). Articulation section (64) further includes a pair of articulation bands (74) extending along a pair of respective channels (76) collectively defined through links (68, 70, 72). Links (68, 70, 72) are generally configured to pivot relative to each other upon actuation of articulation bands (74) to thereby bend articulation section (64) with flexible portion (58) of waveguide (56) therein to achieve an articulated state. By way of example only, articulation section (64) may alternatively or additionally be configured in accordance with one or more teachings of U.S. Pat. No. 9,402,682, entitled "Articulation Joint Features for Articulating Surgical Device," issued Aug. 2, 2016, the disclosure of which is incorporated by reference herein. As another merely illustrative example, articulation section (64) may alternatively or additionally be configured in accordance with one or more teachings of U.S. Pat. No. 9,393,037, issued Jul. 19, 2016, entitled "Surgical Instruments with Articulating Shafts," the disclosure of which is incorporated by reference herein and U.S. Pat. No. 9,095,367, issued Aug. 4, 2015, entitled "Flexible Harmonic Waveguides/Blades for Surgical Instruments," the disclosure of which is incorporated by reference herein. In addition to or in lieu of the foregoing, articulation section (64) and/or may be constructed and/or operable in accordance with at least some of the teachings of U.S. Pat. No. 10,034,683, entitled "Ultrasonic Surgical Instrument with Rigidizing Articulation Drive Members," issued on Jul. 31, 2018. Alternatively, articulation section (64) may be constructed and/or operable in any other suitable fashion.

Links (68, 70, 72) shown in FIGS. 3B-4B pivotally interlock to secure distal shaft portion (62) relative to proximal shaft portion (60) while allowing for deflection of distal shaft portion (62) relative to longitudinal axis (61). In the present example, proximal link (68) is rigidly connected to proximal shaft portion (60) and has a pair of arcuate grooves (78) opposed from each other. Intermediate links (72) respectively have a pair of arcuate tongues (80) proximally extending therefrom and a pair of arcuate grooves (78) positioned distally opposite from respective tongues (80). Each intermediate link (72) has tongues (80) pivotally received within adjacent arcuate grooves (78) of another intermediate link (72) or proximal link (68) as applicable. Distal link (70) is rigidly connected to distal shaft portion (62) and has another pair of arcuate tongues (80) opposed from each other and pivotally received within adjacent arcuate grooves (78) of intermediate link (72). Tongues (80) and grooves (78) connect together to form the series of interlocked links (68, 70, 72).

Figure 4A:
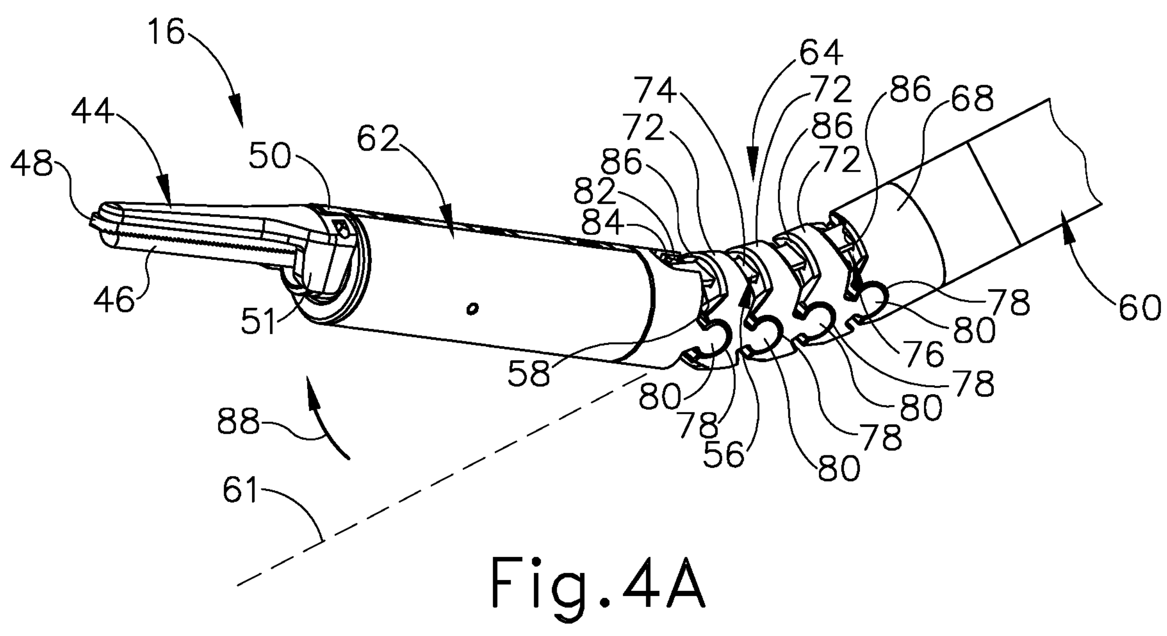
FIG. 4A depicts an enlarged perspective view of the ultrasonic surgical instrument of FIG. 1 with the end effector in a closed position and the shaft assembly in a first articulated configuration.
Figure 4B:
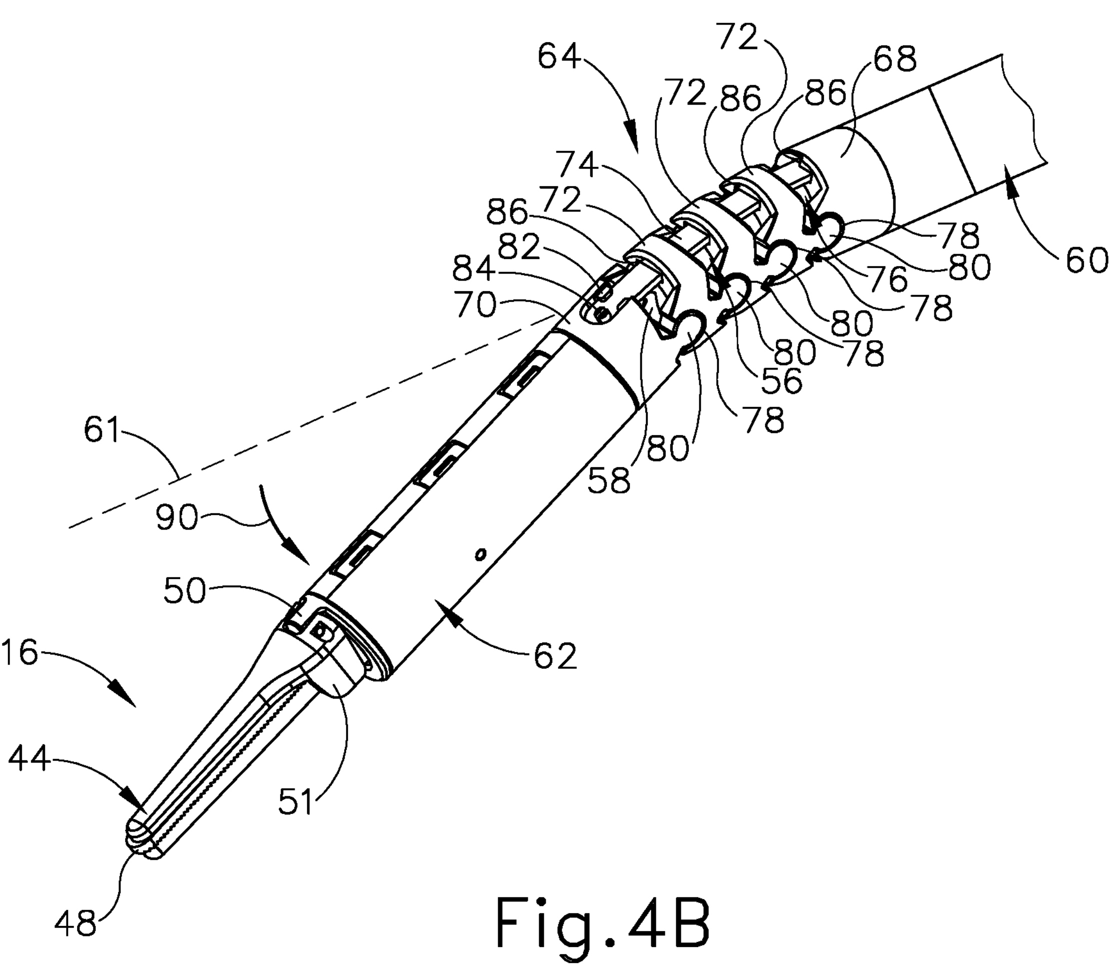
FIG. 4B depicts the enlarged perspective view of the ultrasonic surgical instrument similar to FIG. 4A, but with the shaft assembly in a second articulated configuration.

Distal link (70) further includes a pair of opposing notches (82) with a pin (84) therein configured to receive distal end portions of respective articulation bands (74). More particularly, pins (84) extend through a hole in each respective articulation bands (74) while distal end portions of respective articulation bands (74) are coupled within notches (82). Slots (86) in each of intermediate and proximal links (72, 68) longitudinally align with each other and notches (82) to collectively define channels (76) configured to receive articulation bands (74) while allowing articulation bands (74) to slide relative to links (68, 70, 72). To this end, when articulation bands (74) translate longitudinally in an opposing fashion, this will cause articulation section (64) to bend, thereby laterally deflecting end effector (16) away from the longitudinal axis (61) of proximal shaft portion (60) from a straight configuration as shown in FIG. 3B to a first articulated configuration as shown in FIG. 4A and indicated by an arrow (88) or a second articulated configuration as shown in FIG. 4B and indicated by an arrow (90). In particular, end effector (16) will be articulated toward the articulation band (74) that is being pulled proximally. During such articulation, the other articulation band (74) may be pulled distally. Alternatively, the other articulation band (74) may be driven distally by an articulation control. Furthermore, flexible acoustic waveguide (56) is configured to effectively communicate ultrasonic vibrations from waveguide (56) to blade (46) even when articulation section (64) is in an articulated configuration as shown in FIGS. 4A-4B.

C. Exemplary Base Assembly with Instrument Actuators for Robotic Interface

Figure 5:
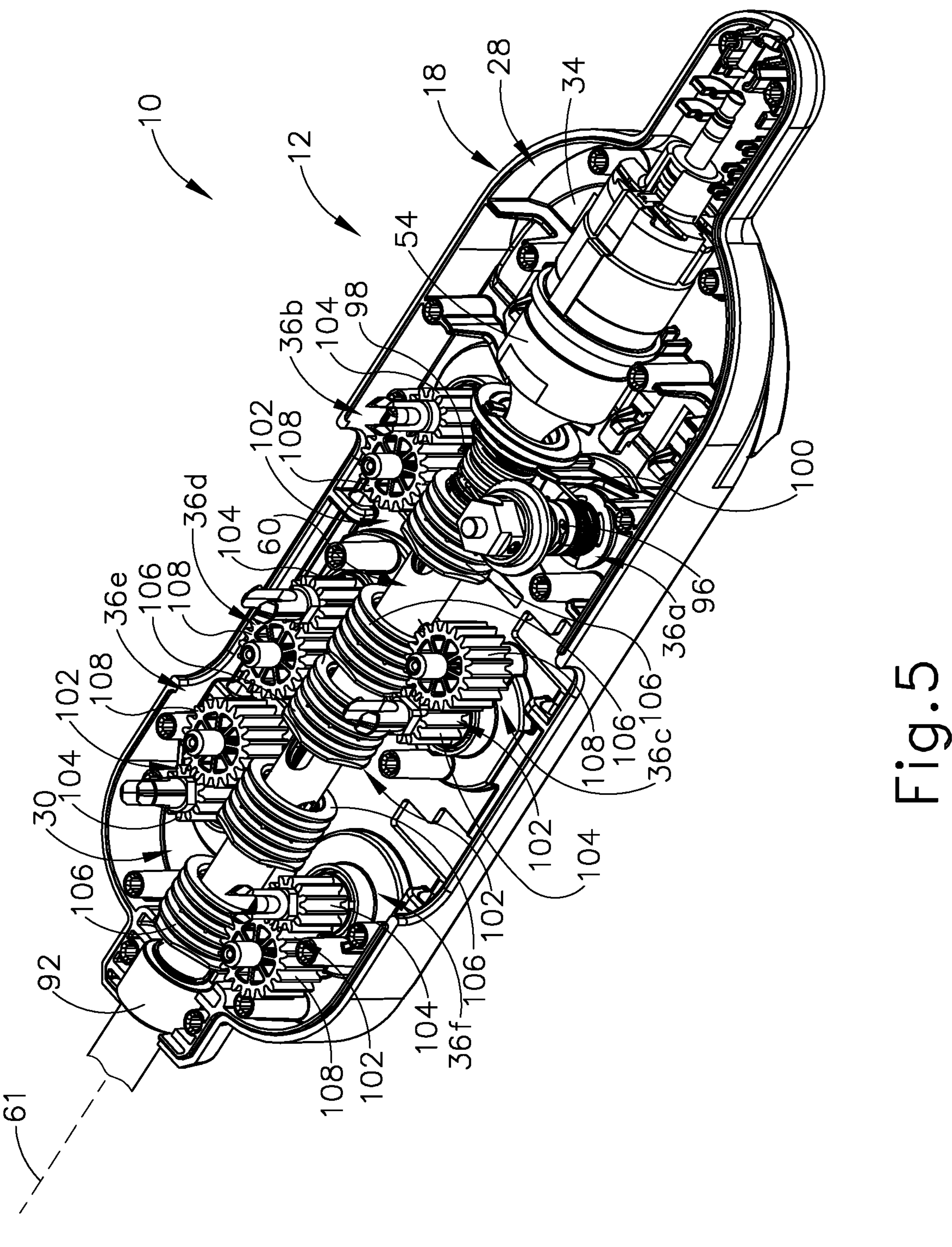
FIG. 5 depicts an enlarged perspective view of the ultrasonic surgical instrument of FIG. 1 with the base assembly having various components removed for greater clarity of an interior space of the base assembly.

FIG. 5 shows interior space (30) of base assembly (12) with instrument actuators (36*a*, 36*b*, 36*c*, 36*d*, 36*e*, 36*f*) in greater detail. Generally, instrument actuators (36*a*, 36*b*, 36*c*, 36*d*, 36*e*, 36*f*) are engaged with shaft assembly (14) and configured to direct movement of end effector (16) and/or shaft assembly (14), such as movement indicated above in one example by arrows (52, 53, 66, 88, 90) (see FIGS. 3A-4B). Shaft assembly (14) is received within base assembly (12) and supported by bearings (92) therein to operatively connect each respective instrument actuator (36*a*, 36*b*, 36*c*, 36*d*, 36*e*, 36*f*) to shaft assembly (14) as well as operatively connect acoustic waveguide (56) (see FIG. 3A) to transducer assembly (54) and a generator (not shown) of the acoustic drivetrain. More particularly, transducer assembly (54) is coupled with generator (not shown) such that transducer assembly (54) receives electrical power from generator (not shown). Piezoelectric elements (not shown) in transducer assembly (54) convert that electrical power into ultrasonic vibrations. Generator (not shown) may be coupled to the electrical power source (not shown) via electrical plug (42) (see FIG. 1) and a control module (not shown) that are configured to provide a power profile to transducer assembly (54) that is particularly suited for the generation of ultrasonic vibrations through transducer assembly (54). By way of example only, generator (not shown) may comprise a GEN04 or GEN11 sold by Ethicon Endo-Surgery, Inc. of Cincinnati, Ohio. In addition or in the alternative, generator (not shown) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Still other suitable forms that generator (not shown) may take, as well as various features and operabilities that generator (not shown) may provide, will be apparent to those of ordinary skill in the art in view of the teachings herein.

Figure 6:
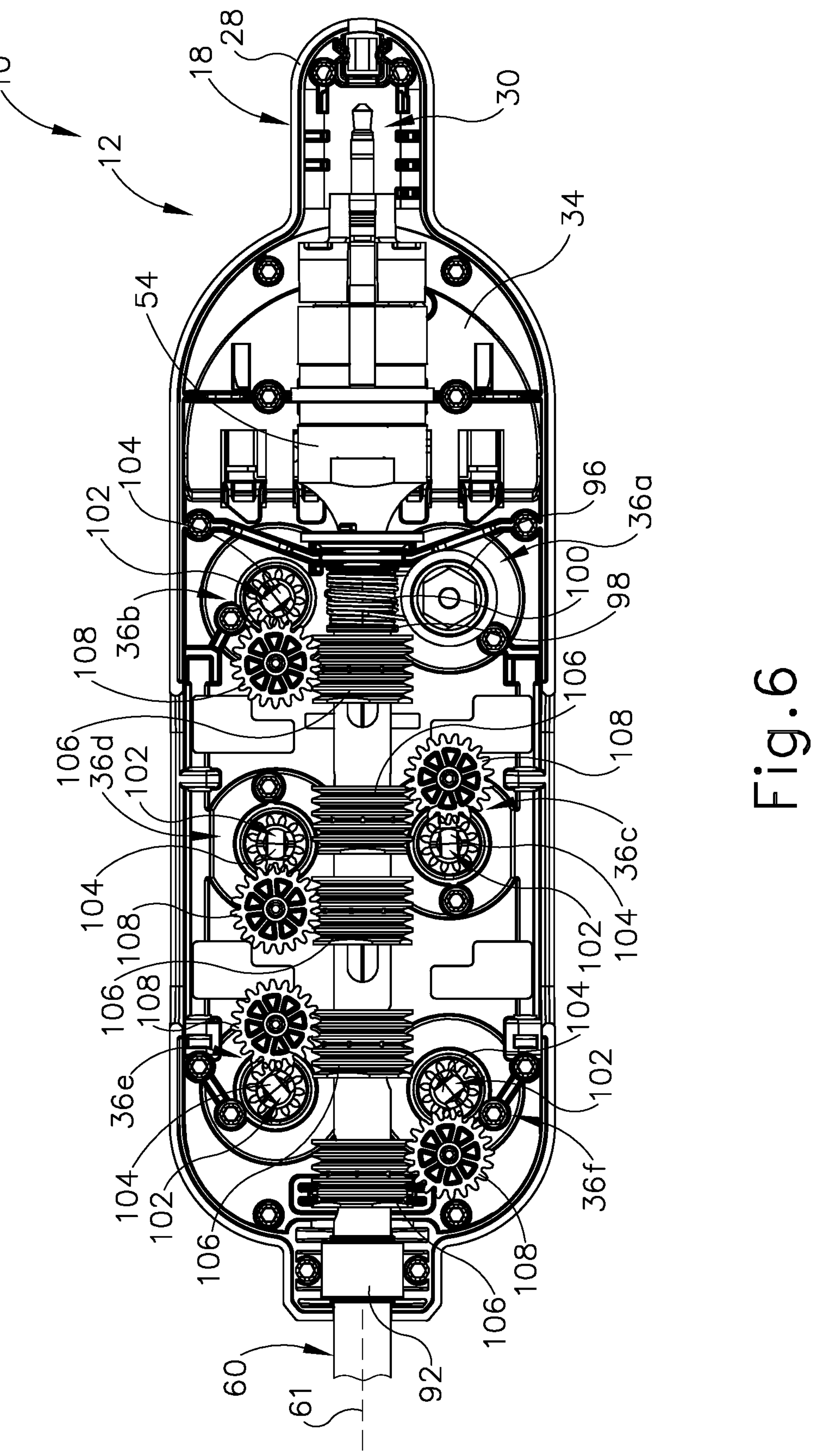
FIG. 6 depicts an enlarged front view of the ultrasonic surgical instrument of FIG. 1 with the base assembly having various components removed for greater clarity of the interior space of the base assembly.

The present example of base assembly (12) shown in FIGS. 5-6 includes six instrument actuators (36*a*, 36*b*, 36*c*, 36*d*, 36*e*, 36*f*), although it will be appreciated that any such number of such instrument actuators (36*a*, 36*b*, 36*c*, 36*d*, 36*e*, 36*f*) configured to direct movement of shaft assembly (14) and/or end effector (16) may be similarly used. As shown with respect to operation of ultrasonic surgical instrument (10), instrument actuator (36*a*) is more particularly a roll system actuator (36*a*) configured to rotate shaft assembly (14) about longitudinal axis (61). In contrast, instrument actuators (36*b*, 36*c*, 36*d*, 36*e*, 36*f*) are linear system actuators (36*b*, 36*c*, 36*d*, 36*e*, 36*f*) configured to translationally drive movement of portions of end effector (16) and/or shaft assembly (14) while simultaneously allowing for rotation of shaft assembly (14) via roll system actuator (36*a*).

Roll system actuator (36*a*) in one example includes a drive spool (96) rigidly connected to puck (38*a*) (see FIG. 2) and a driven spool (98) rigidly connected to proximal shaft portion (60) within housing (18). Drive spool (96) is mounted to rotate with puck (38*a*) (see FIG. 2) about a common puck axis, whereas driven spool (98) is mounted to rotate with proximal shaft portion (60) about the longitudinal axis (61). A cable (100) wraps around each of the drive and driven spools (96, 98), accommodating the differing orientation of the puck axis and longitudinal axis (61), such that rotating drive spool (96) via puck (38*a*) (see FIG. 2) urges rotation of driven spool (98). In turn, shaft assembly (14), including proximal and distal shaft portions (60, 62) rotates about longitudinal axis (61) as indicated by arrow (66) (see FIG. 3A), such as by robotically driven actuation of puck (38*a*) (see FIG. 2).

Linear system actuators (36*b*, 36*c*, 36*d*, 36*e*, 36*f*) of the present example include a gear-rack mechanism (102) having a rotatable drive gear (104), a translatable rack gear (106), and an idler gear (108) connected therebetween. Drive gears (104) are respectively connected to and rigidly project from pucks (38*b*, 38*c*, 38*d*, 38*e*, 38*f*) (see FIG. 2), whereas each rack gear (106) is connected to another portion of proximal shaft portion (60) directing movement of shaft assembly (14) and/or end effector (16) as discussed above. Each rack gear (106) is cylindrical and rigidly connected relative to proximal shaft portion (60) to rotate therewith. Rack gear (106) is thereby configured to rotate with shaft assembly (14) while remaining meshed with idler gear (108). Rotating respective pucks (38*b*, 38*c*, 38*d*, 38*e*, 38*f*) (see FIG. 2) thus respectively rotates drive gears (104) and idler gears (108) to translate rack gears (106) as desired.

In the present example, with respect to FIGS. 2-4B and FIG. 6, linear system actuator (36*b*) has puck (38*b*) operatively connected to clamp arm (44) to direct movement of clamp arm (44) between the open and closed positions according to arrow (52). Linear systems (36*c*, 36*d*) have respective pucks (38*c*, 38*d*) operatively connected to clamp arm (44) to direct movement of clamp arm (44) around blade (46) in both the clockwise and counterclockwise directions according to arrow (53). In addition, linear system actuators (36*e*, 36*f*) have respective pucks (38*e*, 38*f*) operatively connected to articulation bands (74) to direct movement of articulation section (64) according to arrows (88, 90) for deflecting end effector (16) relative to longitudinal axis (61). Of course, in other examples, instrument actuators (36*a*, 36*b*, 36*c*, 36*d*, 36*e*, 36*f*) may be alternatively configured with more or less actuators (36*a*, 36*b*, 36*c*, 36*d*, 36*e*, 36*f*) and/or more or less movement as desired. The invention is thus not intended to be unnecessarily limited to instrument actuators (36*a*, 36*b*, 36*c*, 36*d*, 36*e*, 36*f*) or particular movements of shaft assembly (14) and/or end effector (16) as described in the present example.

II. Exemplary Translatable Rack Gear Assemblies

In some instances, it may be desirable to accommodate for manufacturing tolerances associated with assembly of surgical instrument (10). It may also be desirable to interchange a variety of drive bands and/or articulation bands (74) with a universal translatable rack gear (106) of linear system actuator (36*b*, 36*c*, 36*d*, 36*e*, 36*f*) to provide for greater flexibility and/or customization of surgical instrument (10). Accordingly, exemplary translatable rack gear assemblies (206*b*, 206*c*, 206*d*, 206*e*, 206*f*) are described below with respect FIGS. 7-33, each having rack gear (106) and an anchor (220) configured to receive one or more insert (230). Each insert (230) is then configured to receive a select type of band of shaft assembly (14) for driving movement of a select one of end effector (16) and shaft assembly (14). Thereby, translatable rack gear assemblies (206*b*, 206*c*, 206*d*, 206*e*, 206*f*) are respectively configured to be adjusted to a desired tension for accommodating manufacturing tolerances and/or provide for greater flexibility in assembling and/or operating the surgical instrument.

Figures 7, 8:
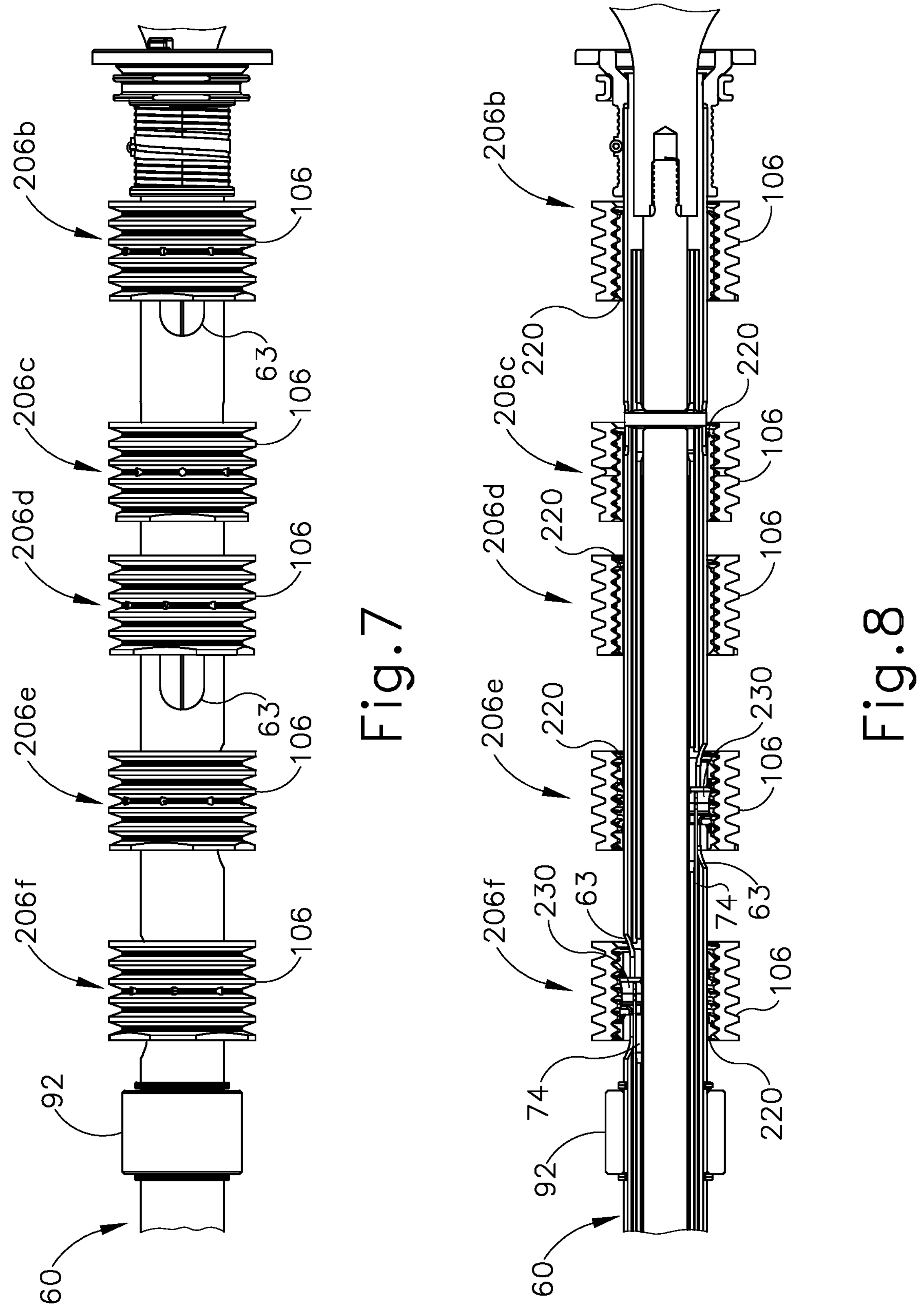
FIG. 7 depicts an enlarged front view of a proximal shaft portion of the ultrasonic surgical instrument of FIG. 1 assembled with a plurality of exemplary translatable rack gear assemblies.
FIG. 8 depicts an enlarged cross-sectional view of the proximal shaft portion of FIG. 7 taken along a centerline thereof.
Figure 9:
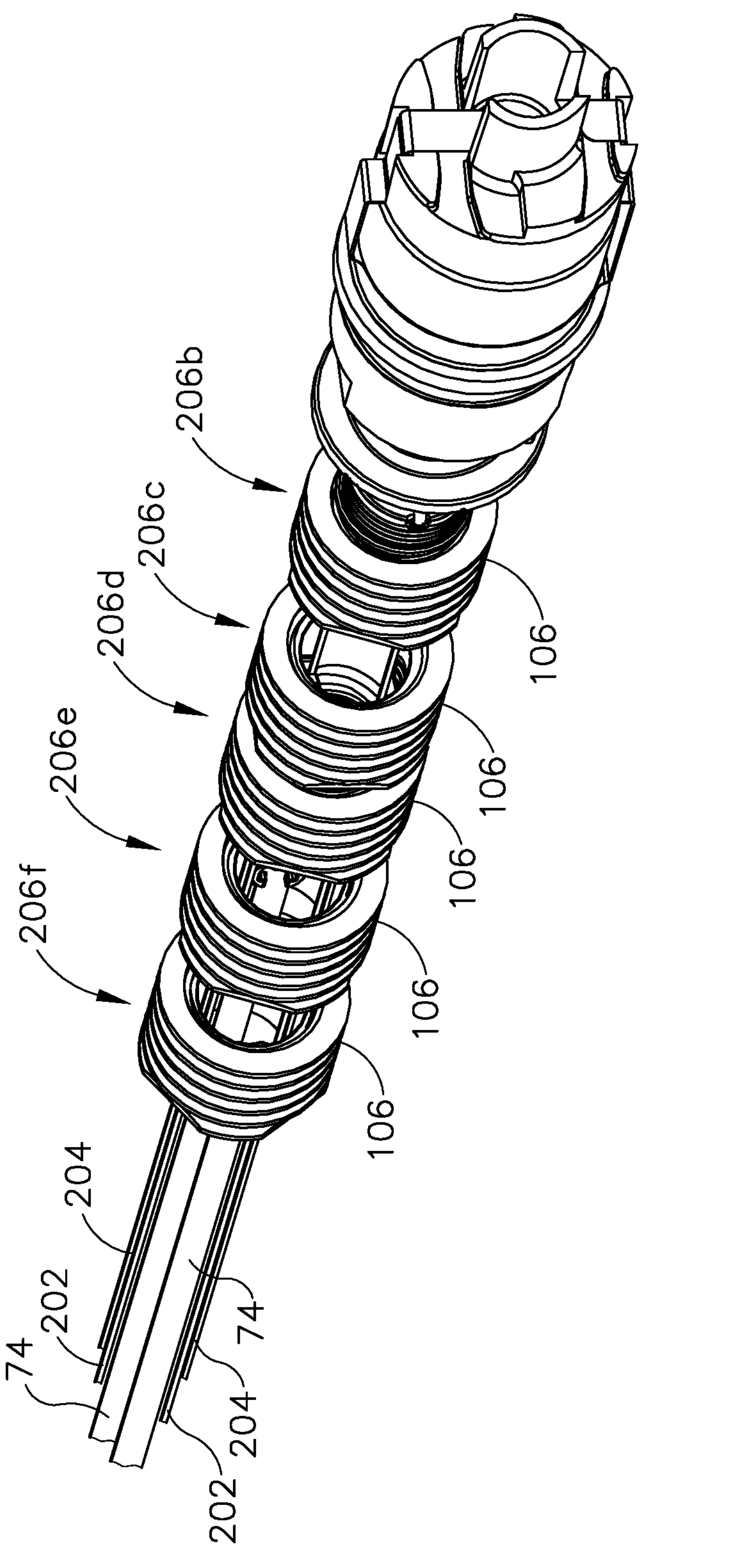
FIG. 9 depicts an enlarged perspective view of the proximal shaft portion of FIG. 7 with the proximal shaft portion having various components removed for greater clarity.
Figure 10:
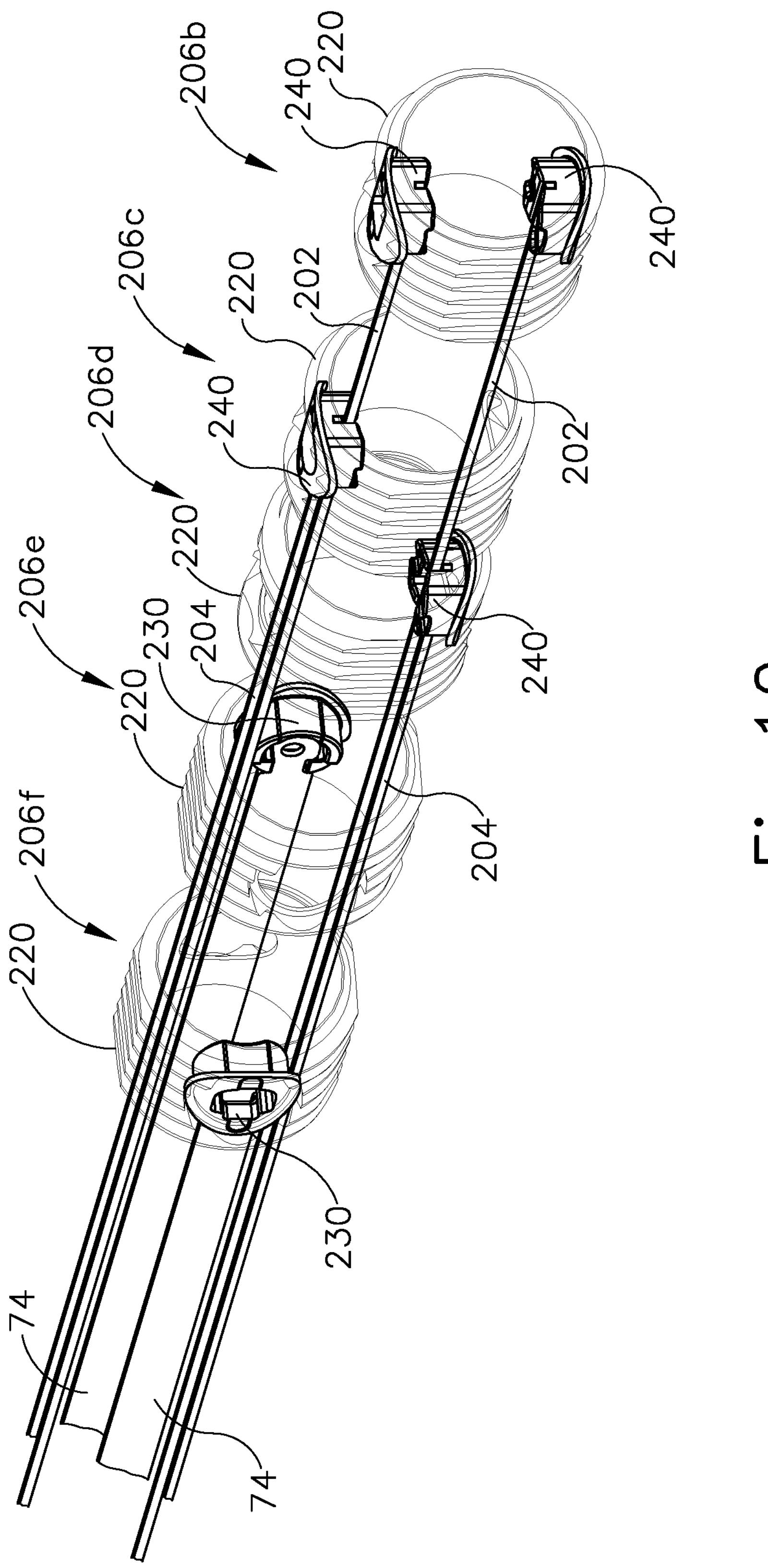
FIG. 10 depicts an enlarged perspective view of the proximal shaft portion of FIG. 7 with the proximal shaft portion and the plurality of translatable rack gear assemblies having various components removed for greater clarity.
Figure 11:
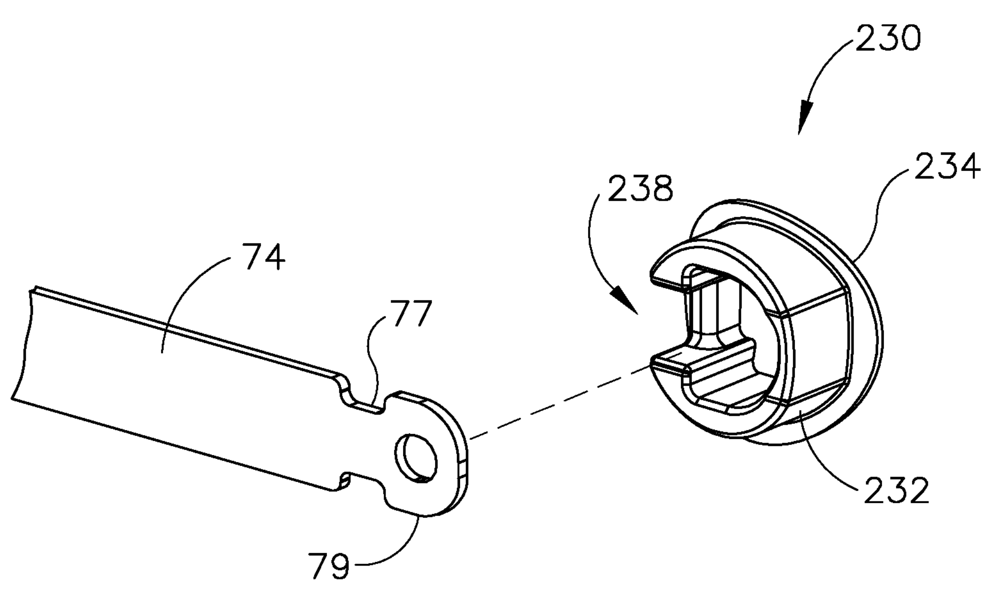
FIG. 11 depicts an exploded perspective view of a proximal end portion of an articulation band of the proximal shaft portion of FIG. 7 and an articulation band insert of the translatable rack gear assembly.
Figure 12:
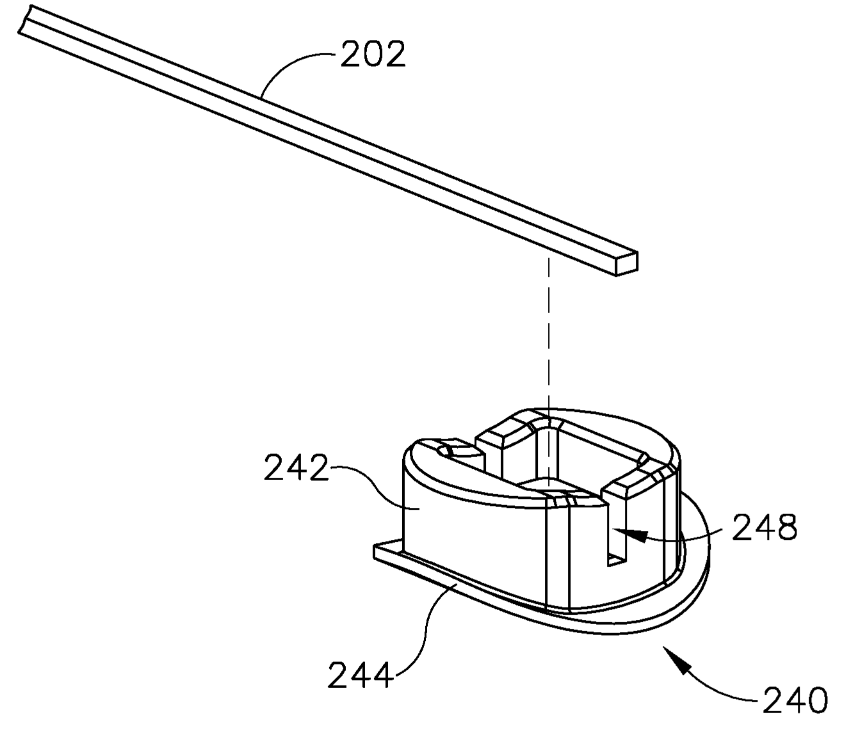
FIG. 12 depicts an exploded perspective view of a proximal end portion of a drive band of the proximal shaft portion of FIG. 7 and a drive band insert of the translatable rack gear assembly.

Referring to FIGS. 7-8, proximal shaft portion (60) of surgical instrument (10) (see FIG. 1) is shown assembled with translatable rack gears (106) as a portion of a plurality of exemplary translatable rack gear assemblies (206*b*, 206*c*, 206*d*, 206*e*, 206*f*). Translatable rack gear assemblies (206*b*, 206*c*, 206*d*, 206*e*, 206*f*) are assembled with proximal shaft portion (60) such that each translatable rack gear assembly (206*b*, 206*c*, 206*d*, 206*e*, 206*f*) is positioned about proximal shaft portion (60) to couple proximal shaft portion (60) with corresponding instrument actuators (36*a*, 36*b*, 36*c*, 36*d*, 36*e*, 36*f*) (see FIG. 6). For instance, as shown in FIGS. 9-10, translatable rack gear assembly (206*b*) is connected with a pair of drive bands (202) and is couplable with linear system actuator (36*b*) (see FIG. 6) to direct movement of clamp arm (44) (see FIG. 1) between the open and closed positions. Each translatable rack gear assembly (206*c*, 206*d*) is connected with a drive band (204) and is couplable with a linear system (36*c*, 36*d*) (see FIG. 6) to direct movement of clamp arm (44) (see FIG. 1) around blade (46) (see FIG. 1) in both the clockwise and counterclockwise directions. Each translatable rack gear assembly (206*e*, 206*f*) is connected with articulation band (74) and is couplable with linear system actuator (36*e*, 36*f*) (see FIG. 6) to direct movement of articulation section (64) (see FIG. 1) for deflecting end effector (16) (see FIG. 1) relative longitudinal axis (61) (see FIGS. 3A-3B). Accordingly, each translatable rack gear assembly (206*b*, 206*c*, 206*d*, 206*e*, 206*f*) comprises one or more of articulation band insert (230) for receiving a proximal end portion of articulation band (74) as shown in FIG. 11 and/or drive band insert (240) for receiving a proximal end portion of drive band (202) as shown in FIG. 12.

Figure 13:
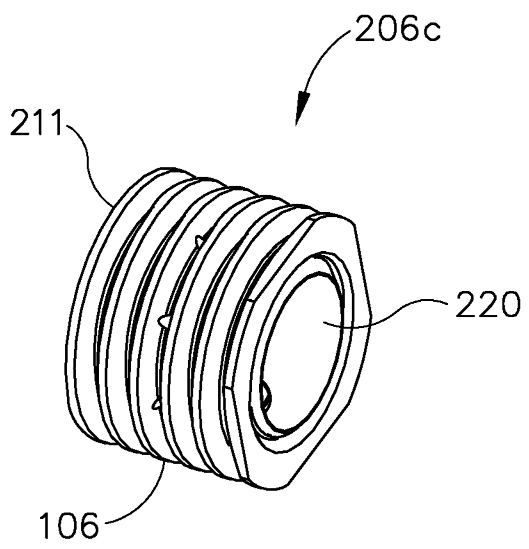
FIG. 13 depicts a perspective view of the translatable rack gear assembly of FIG. 7.
Figure 14:
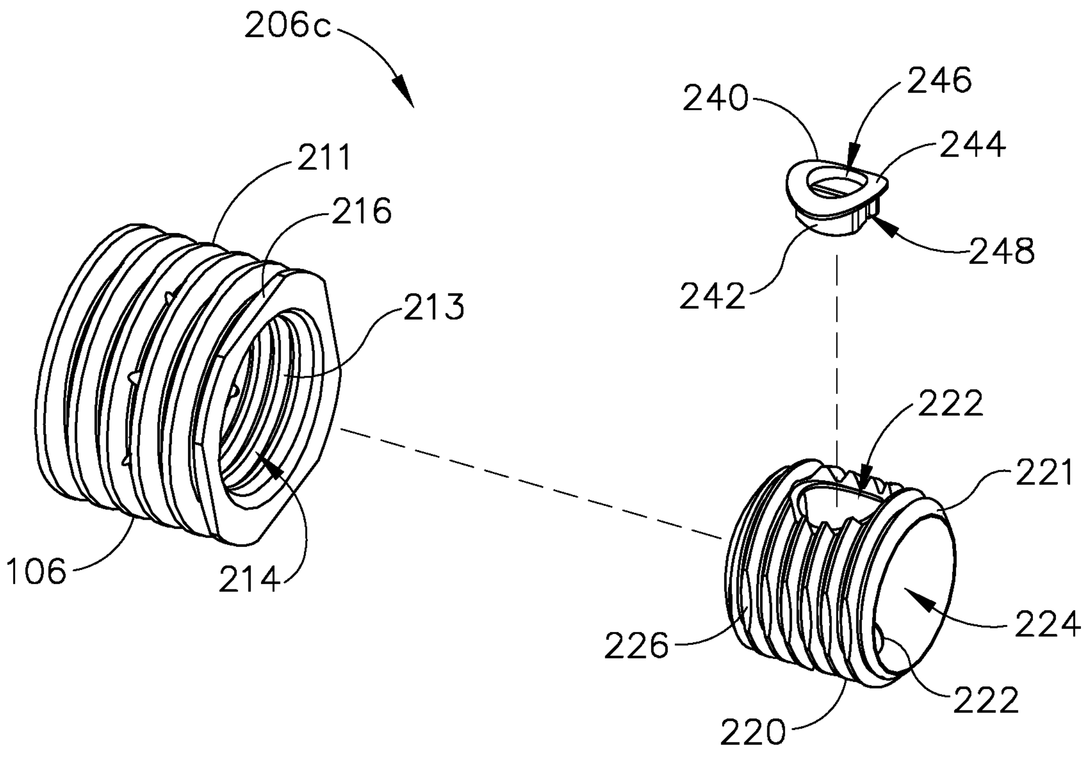
FIG. 14 depicts an exploded perspective view of the translatable rack gear assembly of FIG. 13.

For illustrative purposes, translatable rack gear assembly (206*c*) is shown in FIGS. 13-14 and described below. It should be noted that translatable rack gear assemblies (206*b*, 206*d*, 206*e*, 206*f*) (see FIG. 9) are similar to translatable rack gear assembly (206*c*) such that the description of translatable rack gear assembly (206*c*) would also apply to any of translatable rack gear assemblies (206*b*, 206*d*, 206*e*, 206*f*) in the present example. Referring to FIGS. 13-14, translatable rack gear assembly (206*c*) is shown comprising rack gear (106), an anchor (220) positioned concentrically within rack gear (106), and a drive band insert (240) positioned within anchor (220). For instance, FIGS. 14-18 show translatable rack gear assembly (206*c*) with rack gear (106) removed. As shown, drive band insert (240) is positioned through an opening (222) of the sidewall of anchor (220) to extend within anchor (220). While translatable rack gear assembly (206*c*) is shown having one drive band insert (240), translatable rack gear assembly (206*c*) may include one or more of articulation band inserts (230) and/or drive band inserts (240) as will be described in more detail below.

Figures 19, 20, 21:
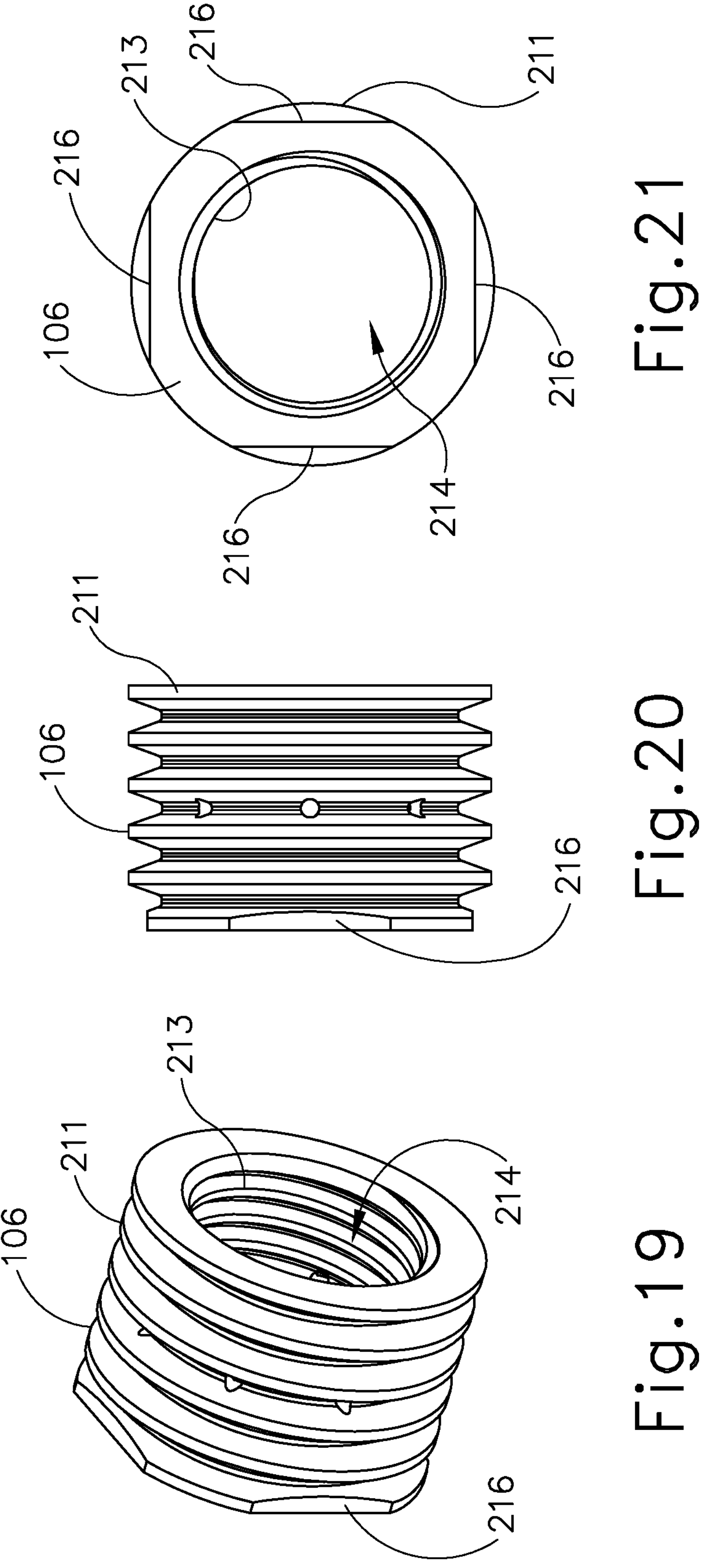
FIG. 19 depicts a perspective view of a rack gear of the translatable rack gear assembly of FIG. 7.
FIG. 20 depicts a front view of the rack gear of FIG. 19.
FIG. 21 depicts a side elevational view of the rack gear of FIG. 19.
Figure 31:
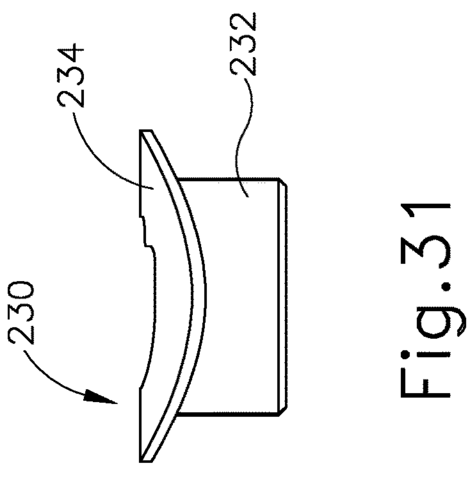
FIG. 31 depicts a front view of the articulation band insert of FIG. 30.
Figure 33:
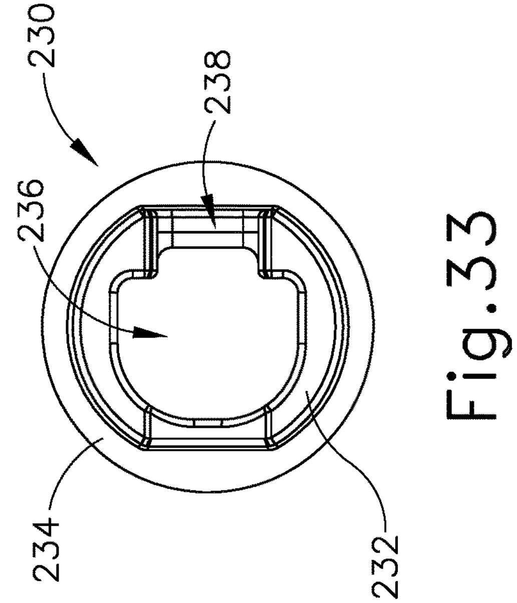
FIG. 33 depicts a plan view of the articulation band insert of FIG. 30.
Figure 30:
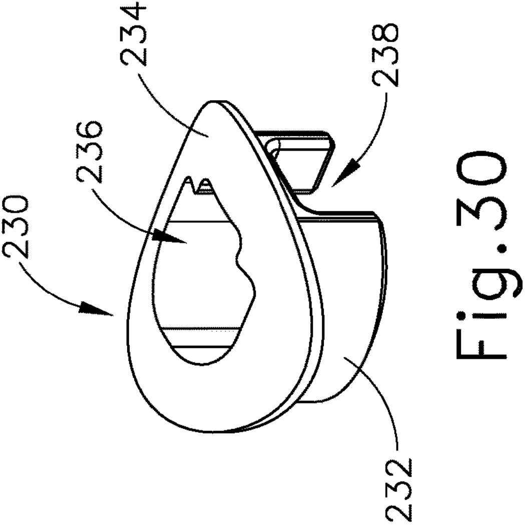
FIG. 30 depicts a perspective view of the articulation band insert of the translatable gear assembly of FIG. 7.
Figure 32:
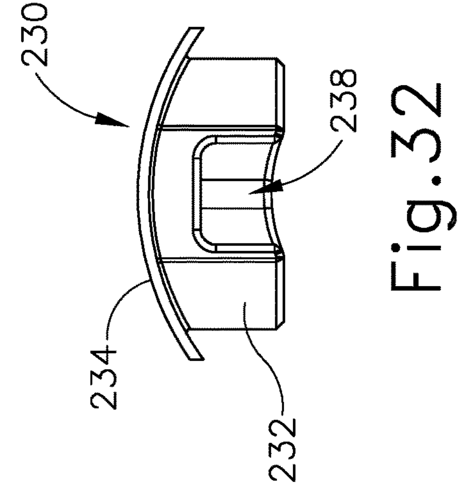
FIG. 32 depicts a side elevational view of the articulation band insert of FIG. 30.

FIGS. 19-21 show rack gear (106) of translatable rack gear assembly (206*c*) (see FIG. 14) in more detail. Rack gear (106) is substantially cylindrical and defines a conduit (214) extending longitudinally through rack gear (106). Rack gear (106) includes splines (211) positioned on an exterior surface of rack gear (106) and an interior threading (213) positioned on an interior surface of rack gear (106) within conduit (214). Accordingly, splines (211) of rack gear (106) are configured to mesh with idler gear (108) (see FIG. 6) and interior threading (213) is configured to mesh with anchor (220) (see FIG. 13). In the illustrated embodiment, a spline (211) on one end of rack gear (106) includes a plurality of substantially flat surfaces (216) positioned about rack gear (106). Flat surfaces (216) may be configured as an engagement surface for grasping during assembly of rack gear (106). While the illustrated embodiment shows four flat surfaces (216) positioned equidistantly about an end spline (211) of rack gear (106), any other suitable number of flat surfaces (216) may be used in any other suitable position about any of splines (211). Rack gear (106) thereby rotates with shaft assembly (14) while remaining meshed with idler gear (108) during rotation of shaft assembly (14) (see FIGS. 1 and 6). Rotating respective pucks (38*b*, 38*c*, 38*d*, 38*e*, 38*f*) (see FIG. 2) thus respectively rotates drive gears (104) and idler gears (108) to translate rack gears (106) as desired.

FIGS. 22-25 show anchor (220) of translatable rack gear assembly (206*c*) (see FIG. 14) in more detail. Anchor (220) is substantially cylindrical and defines a conduit (224) extending longitudinally through anchor (220). A pair of openings (222) extend through opposing sidewall surfaces of anchor (220) such that openings (222) extend from an exterior surface of anchor (220) to conduit (224). Accordingly, anchor (220) may receive a select one of articulation band insert (230) (see FIGS. 11-12) or drive band insert (240) (see FIGS. 11-12) within one or both of openings (222). Each insert (230, 240) (see FIGS. 11-12) is removably coupled with anchor (220) within opening (222) such that inserts (230, 240) (see FIGS. 11-12) are interchangeable. The exterior surface of anchor (220) further comprises threading (221) configured to be received against interior threading (213) (see FIG. 19) of rack gear (106) such that anchor (220) rotates simultaneously with rack gear (106) during rotation of shaft assembly (14) (see FIG. 1) in use. In the illustrated embodiment, each thread (221) of anchor (220) includes a plurality of substantially flat surfaces (226) positioned about anchor (220). Flat surfaces (226) may be configured as an engagement surface for grasping during assembly of anchor (220). While the illustrated embodiment shows two flat surfaces (226) positioned equidistantly about each thread (221) of anchor (220), any other suitable number of flat surfaces (226) may be used in any other suitable position about any of threads (221).

Drive band insert (240) is shown in FIGS. 26-29. Drive band insert (240) comprises a body (242) having a channel (248) extending inwardly and longitudinally through a first end of body (242). Channel (248) is configured to receive a proximal end portion of drive band (202, 204) (see FIG. 12) within channel (248). Accordingly, channel (248) may be sized to correspond to an outer diameter of drive band (202, 204) such that that drive band (202, 204) is inserted within channel (248) with a friction fit to maintain the position of drive band (202, 204) relative to drive band insert (240). Still other suitable configurations for inserting drive band (202, 204) within drive band insert (240) will be apparent to one of ordinary skill in the art in view of the teachings herein. An opposing second end of body (242) of drive band insert (240) then comprises an arcuate flange (244) extending outward from body (242). Arcuate flange (244) is curved to correspond to an exterior surface of anchor (220) (see FIG. 15) when drive band insert (240) is recessed within opening (222) (see FIG. 22) of anchor (220) (see FIG. 15). Body (242) of drive band insert (240) may be inserted within opening (222) (see FIG. 15) of anchor (220) (see FIG. 15) with a friction fit to maintain the position of drive band insert (240) relative to anchor (220) (see FIG. 15). Still other suitable configurations for inserting drive band insert (240) within anchor (220) (see FIG. 15) will be apparent to one of ordinary skill in the art in view of the teachings herein. Arcuate flange (244) of drive band insert (240) defines an opening (246) extending through arcuate flange (244) to channel (248). Accordingly, the proximal end portion of drive band (202, 204) (see FIG. 12) inserted within drive band insert (240) may be externally accessed through opening (246) to adjust drive band (202, 204) (see FIG. 12) as desired.

Articulation band insert (230) is shown in FIGS. 30-33. Articulation band insert (230) comprises a body (232) having a channel (238) extending inwardly and longitudinally through a first end of body (232). An opposing second end of body (232) of articulation band insert (230) then comprises an arcuate flange (234) extending outward from body (232). Arcuate flange (234) is curved to correspond to an exterior surface of anchor (220) (see FIG. 22) when drive band insert (230) is recessed within opening (222) (see FIG. 22) of anchor (220) (see FIG. 22). Body (232) of articulation band insert (230) may be inserted within opening (222) (see FIG. 22) of anchor (220) (see FIG. 22) with a friction fit to maintain the position of articulation band insert (230) relative to anchor (220) (see FIG. 22). Still other suitable configurations for inserting articulation band insert (230) within anchor (220) (see FIG. 22) will be apparent to one of ordinary skill in the art in view of the teachings herein. Arcuate flange (234) defines an opening (236) extending through arcuate flange (234) to channel (238). As shown in FIG. 11, proximal end portion (79) of articulation band (74) is inserted within channel (238) of articulation band insert (230) to align proximal end portion (79) of articulation band (74) with opening (236). In the illustrated embodiment, opening (236) has a wider diameter than channel (238) such that channel (238) is configured to receive a recess (77) on each side of proximal end portion (79) of articulation band (74) to maintain the position of articulation band (74) relative to articulation band insert (230). Accordingly, channel (238) may be sized to correspond to a width of articulation band (74) between recesses (77) such that that articulation band (74) is inserted within channel (238) with a friction fit. Still other suitable configurations for inserting articulation band (74) within articulation band insert (230) will be apparent to one of ordinary skill in the art in view of the teachings herein. In addition, articulation band (74) is aligned with opening (236) of articulation band insert (230) such that articulation band (74) may be externally accessed through opening (236).

Referring to FIGS. 1 and 6-15, in use, each translatable rack gear assembly (206*b*, 206*c*, 206*d*, 206*e*, 206*f*) may be assembled with a select one or more inserts (230, 240) to translationally drive movement of select portions of end effector (16) and/or shaft assembly (14) while simultaneously allowing for rotation of shaft assembly (14) as described above. For instance, anchor (220) is positioned about proximal shaft portion (60) to align anchor (220) with an opening (63) of proximal shaft portion (60). An insert (230, 240) may then be positioned within one or both openings (222) of anchor (220) such that flange (234, 244) of insert (230, 240) abuts anchor (220) to align an outer surface of flange (234, 244) with the outer surface of anchor (220). This allows body (232, 242) of insert (230, 240) to extend within conduit (224) of anchor (220) and through opening (63) of proximal shaft portion (60). Insert (**230,

240) can then receive a corresponding drive band (202, 204) or articulation band (74) within channel (238, 248) of insert (230, 240) through conduit (224) of anchor (220). Openings (63) of proximal shaft portion (60) may further allow anchors (220) and inserts (230, 240) to translate within openings (63).

With insert (230, 240) received within anchor (220), anchor (220) is coupled with rack gear (106), such as by threading exterior threads (221) of anchor (220) with interior threads (213) of rack gear (106). Flat surfaces (216, 226) of rack gear (106) and anchor (220) may be grasped during assembly of rack gear (106) and anchor (220) to aid in rotating rack gear (106) and anchor (220) relative to each other. Rotation of rack gear (106) and anchor (220) causes translation of anchor (220) with insert (230, 240) to thereby adjust tension within the corresponding band (74, 202, 204) of shaft assembly (14). Accordingly, translatable rack gear assemblies (206*b*, 206*c*, 206*d*, 206*e*, 206*f*) may accommodate for manufacturing tolerances during assembly of surgical instrument (10) and/or for replacement of components of translatable rack gear assemblies (206*b*, 206*c*, 206*d*, 206*e*, 206*f*). When assembled, rack gear (106) covers openings (222) of anchor (220). Splines (211) of rack gear (106) are then configured to mesh with idler gear (108). Rack gear (106), anchor (220), and insert (230, 240) are configured to simultaneously rotate with shaft assembly (14) while rack gear (106) remains meshed with idler gear (108) to operate linear system actuators (36*b*, 36*c*, 36*d*, 36*e*, 36*f*) configured to translationally drive movement of portions of end effector (16) and/or shaft assembly (14) while simultaneously allowing for rotation of shaft assembly (14) as described above.

In the illustrated embodiment, translatable rack gear assembly (206*b*) comprises a pair of drive band inserts (240) configured to receive drive band (202) in each insert (240). Translatable rack gear assembly (206*b*) is thereby couplable with linear system actuator (36*b*) to direct movement of clamp arm (44) between the open and closed positions via drive bands (202). Each translatable rack gear assembly (206*c*, 206*d*) comprises one drive band insert (240) configured to receive a drive band (204) in each insert (240) of translatable rack gear assemblies (206*c*, 206*d*). Each translatable rack gear assembly (206*c*, 206*d*) is thereby couplable with a respective linear system (36*c*, 36*d*) to direct movement of clamp arm (44) around blade (46) in both the clockwise and counterclockwise directions via drive bands (204). Each translatable rack gear assembly (206*e*, 206*f*) comprises one articulation band insert (230) configured to receive an articulation band (74) in each insert (230) of translatable rack gear assemblies (206*e*, 206*f*). Each translatable rack gear assembly (206*e*, 206*f*) is thereby couplable with a linear system actuator (36*e*, 36*f*) to direct movement of articulation section (64) for deflecting end effector (16) relative longitudinal axis (61) (see FIGS. 3A-3B) via articulation bands (74). Translatable rack gear assemblies (206*b*, 206*c*, 206*d*, 206*e*, 206*f*) thereby provide flexibility by allowing rack gears (106) to be easily coupled to various components of shaft assembly (14). Still other suitable configurations for translatable rack gear assemblies (206*b*, 206*c*, 206*d*, 206*e*, 206*f*) will be apparent to one with ordinary skill in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument, comprising: (a) an end effector including an ultrasonic blade; (b) a shaft assembly proximally extending from the end effector and defining a longitudinal axis, wherein the shaft assembly includes at least one elongate member connected to a select one or both of the end effector and the shaft assembly; and (c) at least one translatable rack gear assembly coupled with the shaft assembly, wherein the at least one translatable rack gear assembly includes: (i) a rack gear having a conduit extending longitudinally therethrough, (ii) an anchor positioned within the conduit of the rack gear, wherein the anchor is configured to be longitudinally adjusted relative to the longitudinal axis and the rack gear, and (iii) an insert received within the anchor, wherein the anchor is coupled with the at least one elongate member such that adjustment of the anchor relative to the rack gear is configured to longitudinally move the insert and the at least one elongate member for adjusting tension of the at least one elongate member.

Example 2

The ultrasonic surgical instrument of Example 1, wherein the rack gear is operatively connected with a drive assembly to translationally drive movement of the select one or both of the end effector and the shaft assembly.

Example 3

The ultrasonic surgical instrument of Example 2, wherein the rack gear includes a plurality of splines configured to be received against the drive assembly such that the rack gear is configured to rotate relative to the drive assembly while remaining coupled with the drive assembly.

Example 4

The ultrasonic surgical instrument of any one or more of Examples 1 through 3, wherein the rack gear includes an interior threading, wherein the anchor includes an exterior threading that corresponds with the interior threading of the rack gear such that rotation of the anchor relative to the rack gear is configured to translate the anchor relative to the rack gear.

Example 5

The ultrasonic surgical instrument of any one or more of Examples 1 through 4, wherein the rack gear and the anchor are rotatable relative to each other, wherein the rack gear includes a plurality of first flat surfaces and the anchor includes a plurality of second flat surfaces such that the plurality of first and second flat surfaces are respectively configured for grasping during rotation of the rack gear relative to the anchor.

Example 6

The ultrasonic surgical instrument of any one or more of Examples 1 through 5, wherein the anchor includes a sidewall and an opening extending through the sidewall.

Example 7

The ultrasonic surgical instrument of any one or more of Examples 1 through 6, wherein the anchor is configured to receive a plurality of the inserts.

Example 8

The ultrasonic surgical instrument of Example 7, wherein the anchor includes a plurality of the openings through the sidewall of the anchor, wherein each of the plurality of the openings is configured to receive the insert.

Example 9

The ultrasonic surgical instrument of any one or more of Examples 1 through 8, wherein the insert includes a body extending within the shaft assembly, the body having an end portion and a channel extending inwardly and longitudinally through the end portion of the body, wherein the channel is configured to receive the at least one elongate member.

Example 10

The ultrasonic surgical instrument of Example 9, wherein the channel is sized to correspond to the at least one elongate member to maintain a position of the at least one elongate member relative to the body of the insert.

Example 11

The ultrasonic surgical instrument of Example 9, wherein the insert includes an opening extending through the body to the channel.

Example 12

The ultrasonic surgical instrument of any one or more of Examples 1 through 11, wherein the insert includes a flange, wherein the flange is recessed within the anchor.

Example 13

The ultrasonic surgical instrument of Example 12, wherein the flange is an arcuate flange, wherein the arcuate flange is curved to correspond to an exterior surface of the anchor.

Example 14

The ultrasonic surgical instrument of any one or more of Examples 1 through 12, wherein the shaft assembly includes an articulation section configured to articulate from a straight configuration to an articulated configuration to thereby deflect the end effector relative to the longitudinal axis, wherein the insert is an articulation band insert, wherein the at least one elongate member is an articulation band configured to drive movement of the articulation section.

Example 15

The ultrasonic surgical instrument of any one or more of Examples 1 through 14, wherein the at least one elongate member is a drive band configured to drive movement of the end effector.

Example 16

A surgical instrument, comprising: (a) an end effector; (b) a shaft assembly proximally extending from the end effector and defining a longitudinal axis, wherein the shaft assembly includes a first elongate member connected to the end effector and a second elongate member connected to the shaft assembly; (c) a first translatable rack gear assembly coupled with the shaft assembly, wherein the first translatable rack gear assembly includes: (i) a first rack gear having a first conduit extending longitudinally therethrough, (ii) a first anchor positioned within the first conduit of the first rack gear, wherein the first anchor is configured to be longitudinally adjusted relative to the longitudinal axis and the first rack gear, and (iii) a first insert received within the first anchor, wherein the first anchor is coupled with the first elongate member such that adjustment of the first anchor relative to the first rack gear is configured to longitudinally move the first insert and the first elongate member for adjusting tension the first elongate member; and (d) a second translatable rack gear assembly coupled with the shaft assembly, wherein the second translatable rack gear assembly includes: (i) a second rack gear having a second conduit extending longitudinally therethrough, (ii) a second anchor positioned within the second conduit of the second rack gear, wherein the second anchor is configured to be longitudinally adjusted relative to the longitudinal axis and the second rack gear, and (iii) a second insert received within the second anchor, wherein the second anchor is coupled with the second elongate member such that adjustment of the second anchor relative to the second rack gear is configured to longitudinally move the second insert and the second elongate member for adjusting tension the second elongate member.

Example 17

The surgical instrument of Example 16, wherein the end effector further includes an ultrasonic blade and a clamp arm movably coupled relative to the ultrasonic blade, wherein the first elongate member is operatively connected between the clamp arm and the first insert for selectively directing movement of the clamp arm via the first translatable rack gear assembly.

Example 18

The surgical instrument of any one or more of Examples 16 through 17, wherein the first anchor has a first sidewall and includes a plurality of first openings extending through the first sidewall configured to respectively receive the first insert, wherein the second anchor has a second sidewall and includes a plurality second openings extending through the second sidewall configured to respectively receive the second insert.

Example 19

The surgical instrument of any one or more of Examples 16 through 18, wherein the shaft assembly further includes an articulation section, wherein the second elongate member is operatively connected between articulation section and the second insert for selectively directing movement of the articulation section via the second translatable rack gear assembly.

Example 20

A method adjusting tension of an elongate member of an ultrasonic surgical instrument, the ultrasonic surgical instrument including (a) an end effector including an ultrasonic blade; (b) a shaft assembly proximally extending from the end effector and defining a longitudinal axis, wherein the shaft assembly includes at least one elongate member connected to a select one or both of the end effector and the shaft assembly; and (c) at least one translatable rack gear assembly coupled with the shaft assembly, wherein the at least one translatable rack gear assembly includes: (i) a rack gear having a conduit extending longitudinally therethrough, (ii) an anchor positioned within the conduit of the rack gear, wherein the anchor is configured to be longitudinally adjusted relative to the longitudinal axis and the rack gear, and (iii) an insert received within the anchor, wherein the anchor is coupled with the at least one elongate member such that adjustment of the anchor relative to the rack gear is configured to longitudinally move the insert and the at least one elongate member for adjusting tension of the at least one elongate member, the method comprising: (a) selectively rotating the anchor relative to the rack gear thereby translating the insert with the elongate member thereby adjusting tension in the elongate member.

IV. Miscellaneous

Any one or more of the teaching, expressions, embodiments, examples, etc. described herein may be combined with any one or more of the teachings, expressions, embodiments, examples, etc. described in U.S. patent application Ser. No. 16/556,661, entitled "Ultrasonic Surgical Instrument with a Multi-Planar Articulating Shaft Assembly," filed on Aug. 30, 2019, published as U.S. Pub. No. 2021/0059709 on Mar. 4, 2021; U.S. patent application Ser. No. 16/556,667, entitled "Ultrasonic Transducer Alignment of an Articulating Ultrasonic Surgical Instrument," filed on Aug. 30, 2019, issued as U.S. Pat. No. 11,612,409 on Mar. 28, 2023; U.S. patent application Ser. No. 16/556,625, entitled "Ultrasonic Surgical Instrument with Axisymmetric Clamping," filed on Aug. 30, 2019, issued as U.S. Pat. No. 11,471,181 on Oct. 18, 2022; U.S. patent application Ser. No. 16/556,635, entitled "Ultrasonic Blade and Clamp Arm Alignment Features," filed on Aug. 30, 2019, issued as U.S. Pat. No. 11,457,945 or Oct. 4, 2022. The disclosure of each of these applications is incorporated by reference herein.

It should be understood that any of the versions of instruments described herein may include various other features in addition to or in lieu of those described above. By way of example only, in addition to the teachings above, it should be understood that the instruments described herein may be constructed and operable in accordance with at least some of the teachings of U.S. Pat. Nos. 5,322,055; 5,873,873; 5,980,510; 6,325,811; 6,773,444; 6,783,524; 9,095,367; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pat. No. 8,623,027, issued Jan. 7, 2014; U.S. Pat. No. 9,023,071, issued May 5, 2015; U.S. Pat. No. 8,461,744, issued Jun. 11, 2013; U.S. Pat. No. 9,381,058, issued Jul. 5, 2016; U.S. Pub. No. 2012/0116265, now abandoned; U.S. Pat. No. 9,393,037, issued Jul. 19, 2016; U.S. Pat. No. 10,172,636, issued Jan. 8, 2019; and/or U.S. Pat. App. No. 61/410,603. The disclosures of each of the foregoing patents, publications, and applications are incorporated by reference herein. It should also be understood that the instruments described herein may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, the instruments described herein may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the teachings herein relating to the instruments described herein, there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into another example of a robotic surgical system, and those of ordinary skill in the art will recognize that various teachings herein may be readily combined with various teachings of any of the following: U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S.

Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:

(a) an end effector;

(b) a shaft assembly proximally extending from the end effector and defining a longitudinal axis, wherein the shaft assembly includes a first elongate member connected to a select one or both of the end effector and the shaft assembly; and (c) a first actuator operatively connected to the shaft assembly, including:

(i) a first driven portion configured to be translatably driven by a first drive portion, and (ii) a first adjustable coupling configured to selectively couple the first elongate member in tension relative to the first driven portion in a select one of a first proximal position and a first distal position, wherein the first elongate member coupled in the first distal position has relatively less tension, and wherein the first elongate member coupled in the first proximal position has relatively more tension, wherein the first driven portion has a conduit longitudinally extending therethrough, and wherein the first adjustable coupling includes an anchor received within the conduit, and wherein the anchor is configured to be longitudinally adjusted relative to the driven portion.

2. The surgical instrument of claim 1, further comprising an acoustic waveguide, wherein the acoustic waveguide extends through the first driven portion.

3. The surgical instrument of claim 1, wherein the first driven portion is configured to be longitudinally driven by the first drive portion.

4. The surgical instrument of claim 1, wherein the first driven portion has a first rack gear.

5. The surgical instrument of claim 1, wherein the first adjustable coupling further includes an insert received within the anchor, wherein the first elongate member is coupled with the insert such that adjustment of the anchor relative to the first driven portion is configured to longitudinally move the insert and the first elongate member for adjusting tension of the first elongate member.

6. The surgical instrument of claim 5, wherein the insert includes a body extending within the shaft assembly, the body having an end portion and a channel extending inwardly and longitudinally through the end portion of the body, wherein the channel is configured to receive the first elongate member.

7. The surgical instrument of claim 6, wherein the channel is sized to correspond to the first elongate member to maintain coupling of the first elongate member relative to the body of the insert.

8. The surgical instrument of claim 6, wherein the insert includes an opening extending through the body to the channel.

9. The surgical instrument of claim 5, wherein the insert includes a flange, wherein the flange is recessed within the anchor.

10. The surgical instrument of claim 9, wherein the flange is an arcuate flange, wherein the arcuate flange is curved to correspond to an exterior surface of the anchor.

11. The surgical instrument of claim 1, wherein the first driven portion includes an interior threading, wherein the anchor includes an exterior threading that corresponds with the interior threading of the first driven portion such that rotation of the anchor relative to the first driven portion is configured to translate the anchor relative to the first driven portion.

12. The surgical instrument of claim 1, wherein the first driven portion and the anchor are rotatable relative to each other, wherein the first driven portion includes a plurality of first flat surfaces and the anchor includes a plurality of second flat surfaces such that the plurality of first and second flat surfaces are respectively configured for grasping during rotation of the first driven portion relative to the anchor.

13. The surgical instrument of claim 1, wherein the shaft assembly includes an articulation section configured to articulate from a straight configuration to an articulated configuration to thereby deflect the end effector relative to the longitudinal axis, wherein the first elongate member is an articulation band configured to drive movement of the articulation section.

14. The surgical instrument of claim 1, wherein the first elongate member is a drive band configured to drive movement of the end effector.

15. The surgical instrument of claim 1, further comprising:

(a) a second actuator operatively connected to the shaft assembly, including:

(i) a second driven portion configured to be translatably driven by a second drive portion, and (ii) a second adjustable coupling configured to selectively couple the second elongate member in tension relative to the second driven portion in a select one of a second proximal position and a second distal position, wherein the second elongate member coupled in the second distal position has relatively less tension, and wherein the second elongate member coupled in the second proximal position has relatively more tension.

16. The surgical instrument of claim 15, further comprising an acoustic waveguide, wherein the acoustic waveguide extends through the first and second driven portions.

17. A surgical instrument, comprising:

(a) an end effector;

(b) a shaft assembly proximally extending from the end effector and defining a longitudinal axis, wherein the shaft assembly includes a first elongate member connected to a select one or both of the end effector and the shaft assembly; and (c) a first actuator operatively connected to the shaft assembly, including:

(i) a first driven portion configured to be translatably driven by a first drive portion, and (ii) a first adjustable coupling configured to selectively couple the first elongate member in tension relative to the first driven portion in a select one of a first proximal position and a first distal position, wherein the first elongate member coupled in the first distal position has relatively less tension, and wherein the first elongate member coupled in the first proximal position has relatively more tension, wherein the first driven portion has a first rack gear.

18. A surgical instrument, comprising:

(a) an end effector;

(b) a shaft assembly proximally extending from the end effector and defining a longitudinal axis, wherein the shaft assembly includes a first elongate member connected to a select one or both of the end effector and the shaft assembly;

(c) a first actuator operatively connected to the shaft assembly, including:

(i) a first driven portion configured to be translatably driven by a first drive portion, and (ii) a first adjustable coupling configured to selectively couple the first elongate member in tension relative to the first driven portion in a select one of a first proximal position and a first distal position, wherein the first elongate member coupled in the first distal position has relatively less tension, and wherein the first elongate member coupled in the first proximal position has relatively more tension; and (d) a second actuator operatively connected to the shaft assembly, including:

(i) a second driven portion configured to be translatably driven by a second drive portion, and (ii) a second adjustable coupling configured to selectively couple the second elongate member in tension relative to the second driven portion in a select one of a second proximal position and a second distal position, wherein the second elongate member coupled in the second distal position has relatively less tension, and wherein the second elongate member coupled in the second proximal position has relatively more tension.

19. The surgical instrument of claim 18, wherein the first driven portion has a first rack gear.

20. The surgical instrument of claim 19, wherein the second driven portion has a second rack gear.

* * * * *